United States Patent [19]
Kaigler et al.

[11] Patent Number: 5,546,934
[45] Date of Patent: Aug. 20, 1996

[54] RESUSCITATOR

[75] Inventors: William J. Kaigler, North Huntingdon; Richard J. Lordo, West Deer Township, both of Pa.

[73] Assignee: Respironics, Inc., Murrysville, Pa.

[21] Appl. No.: 312,313

[22] Filed: Sep. 26, 1994

[51] Int. Cl.$^6$ ........................................ A62B 7/00
[52] U.S. Cl. .................. 128/205.13; 285/45; 285/98; 285/110; 285/175; 285/235; 285/281; 285/423; 285/921
[58] Field of Search ......................... 285/110, 98, 272, 285/921, 281, 175, 235, 423, 45; 128/205.13

[56] References Cited

U.S. PATENT DOCUMENTS

| | | |
|---|---|---|
| Re. 24,193 | 8/1956 | Emerson . |
| 2,399,643 | 5/1946 | Kreiselman . |
| 2,834,339 | 5/1958 | Bennett et al. . |
| 3,009,459 | 11/1961 | Ruben . |
| 3,196,866 | 7/1965 | Adams . |
| 3,262,446 | 7/1966 | Stoner . |
| 3,291,121 | 12/1966 | Vizneau . |
| 3,316,903 | 5/1967 | Richards . |
| 3,408,091 | 10/1968 | Zylstra .................. 285/110 X |
| 3,473,529 | 10/1969 | Wallace . |
| 3,796,216 | 3/1974 | Schwarz . |
| 3,858,615 | 1/1975 | Weigl . |
| 3,908,704 | 9/1975 | Clement et al. . |
| 4,000,341 | 12/1976 | Matson . |
| 4,037,595 | 7/1977 | Elam . |
| 4,045,055 | 8/1977 | Blakely .................. 285/110 X |
| 4,077,404 | 3/1978 | Elam . |
| 4,088,131 | 5/1978 | Elam et al. . |
| 4,113,288 | 9/1978 | Cox .................... 285/281 X |
| 4,121,580 | 10/1978 | Fabish . |
| 4,266,814 | 5/1981 | Gallagher .............. 285/921 X |
| 4,374,521 | 2/1983 | Nelson et al. . |
| 4,501,271 | 2/1985 | Clifton et al. . |
| 4,747,621 | 5/1986 | Gans et al. ............. 285/921 X |
| 4,770,445 | 9/1988 | Steer et al. ............. 285/110 |
| 4,774,941 | 10/1988 | Cook . |
| 4,821,713 | 4/1989 | Bauman . |
| 4,852,563 | 8/1989 | Gross . |
| 4,852,564 | 8/1989 | Sheridan et al. . |
| 4,917,081 | 4/1990 | Bartos . |
| 4,919,132 | 4/1990 | Miser . |
| 4,938,209 | 7/1990 | Fry . |
| 4,941,689 | 7/1990 | Sjoberg ................. 285/281 X |
| 5,062,420 | 11/1991 | Levine . |
| 5,067,487 | 11/1991 | Bauman . |
| 5,109,840 | 5/1992 | Daleiden . |
| 5,140,982 | 8/1992 | Bauman . |
| 5,279,289 | 1/1994 | Kirk . |

FOREIGN PATENT DOCUMENTS

| | | | |
|---|---|---|---|
| 3235058 | 3/1984 | Germany ............... 285/921 |
| 3710853 | 10/1988 | Germany ............... 285/921 |
| 2181806 | 4/1987 | United Kingdom ....... 285/281 |

*Primary Examiner*—Dave W. Arola
*Attorney, Agent, or Firm*—Reed Smith Shaw & McClay

[57] ABSTRACT

A resuscitator apparatus including a resilient, self-inflating squeeze bag having a single combined inlet/outlet which is preferably removably connected to a first manifold in operative communication with a substantially unbiased valve device. The first manifold includes an inlet coupling adapted for connection to a source of pressurized respiratory gas such as oxygen and an outlet coupling adapted for connection to a first end of a tubular connector. The tubular connector is desirably formed as a short, kink-resistant, flexible hinge member. The second end of the tubular connector is adapted for swiveled connection to an inlet coupling of a second manifold in operative communication with a non-rebreathing valve contained within a tubular, preferably L-shaped housing. The tubular housing includes a first leg connected to the second manifold and a second leg extending substantially perpendicular to the first leg, the second leg being adapted for connection to a subject interface member such as a breathing mask. An oxygen reservoir bag preferably formed of thin, pliable plastic surrounds the tubular connector and is sealingly attached without supplemental fasteners to the first and second manifolds. In the event the oxygen to the first supply manifold should falter, substantially unbiased valve device permits the subject immediate and unrestricted access to atmospheric air.

14 Claims, 18 Drawing Sheets

5,546,934

RESUSCITATOR

FIELD OF THE INVENTION

The present invention relates in general to breathing assistance apparatus and, more particularly, to resuscitator apparatus of the "squeeze bag" type.

BACKGROUND OF THE INVENTION

Resuscitation, as that term is herein used, refers generally to externally exerted efforts to assist or restore breathing of a patient whose natural breathing has either become impaired or has ceased, or to at least temporarily attempt to emulate the effects of more natural breathing in the patient. Resuscitation involves forcing air or oxygen under appropriate pressure through the patient's natural airway system and into his lungs to inflate the latter at appropriate intervals separated by periods during which such application of air or oxygen under pressure is interrupted (and an external physical pressure may be applied to the patient's chest) to permit the previously applied air to escape from the patient's lungs and the latter to deflate.

The forms of previous resuscitators of greatest interest as background for this invention, commonly called "squeeze bag" or "bag-valve-mask" resuscitators, employ some type of manually compressible and self-restoring bag having the interior thereof in fluid communication with a face mask. In its most primitive conceptual form, such a device could be operated for resuscitation purposes simply by applying the mask to the face of a patient, manually squeezing the bag to force air from the bag through the mask and into the patient's lungs, releasing the squeezing pressure from the bag and removing the mask from the patient's face to permit escape of air from the patient's lungs. At the same time, the bag would restore itself and thereby self-inflate with fresh atmospheric air through the mask. The bag would then remain in its restored condition until the next bag squeezing operation and such cycle would be repeated as necessary. A squeeze bag resuscitator thus permits a trained person administering treatment to directly control both the quantity of air forced into the patients lungs and the intervals of doing so to best suit the condition of the patient through choice of the extent and timing of squeezing of the bag.

Even relatively early squeeze bag resuscitators soon incorporated various refinements, including employment of resilient squeeze bags adapted to be conveniently held in one hand with the face masks carried more or less directly on the frontal extremities of the bags to increase portability and facilitate use by a single person. A bag fill valve (an inward flow permitting check valve for communicating the interior of the bag with the atmosphere) was introduced to permit refilling of the bag with fresh air during its restoration phase without removing the mask from the face of the patient. And, in conjunction with the bag fill valve came the evolution of the patient non-rebreathing valve assembly. Such assembly is interposed between the bag and the mask and permits fresh air to move from the bag into the mask during the squeeze phase, but vents to the atmosphere air returned to the mask from the patient's lungs during the bag restoration or restored phases, thereby preventing passage of the expired air into the bag from which it would be forced back into the patients lungs or "rebreathed" during the next squeeze phase.

During the course of development of squeeze bag type resuscitators, it was recognized that it would be desirable to administer oxygen, or at least oxygen enriched air, rather than merely atmospheric air, in treating some resuscitation patients.

Accordingly, the development of practical means for introducing oxygen into the squeeze bag initially entailed providing "oxygen enrichment" for the air drawn into the squeeze bag from the atmosphere during the restoration phase of the bag cycle. A common and still prevalent approach to oxygen enrichment is to provide an elongate tube of relatively large diameter having one end thereof in fluid communication with the fill valve opening of the bag (typically at the extremity of the bag opposite from the non-rebreathing valve and mask) and the other end thereof exposed to the atmosphere, together with a considerably smaller tube extending into the larger tube and coupled with a pressurized oxygen source for continuously releasing oxygen into the air entering and accumulating within the large tube from the atmosphere. Such devices are commonly call "oxygen accumulators" and are effective to introduce a mixture of air reasonably enriched with oxygen into the bag during the restoration phase of its cycle, without significantly increasing the pressure within the bag (since one end of the large tube of the accumulator is in free communication with the atmosphere). Examples of these and other oxygen accumulator resuscitators may be found in U.S. Pat. Nos. 4,501,271, 4,774,941, 4,821,713, 5,067,487, 5,109,840, 5,140,982 and 5,279,289. A notable shortcoming of resuscitators of this sort is that the concentration of the continuously flowing oxygen gas is subject to dilution by the ambient air with which it is mixed.

In the oxygen accumulator resuscitators described in U.S. Pat. Nos. 4,821,713, 5,067,487 and 5,140,982, two discrete, sequentially operable valves are provided to deliver the air/oxygen mixture, first into the tubular member and thereafter into the face mask. Each valve possesses a comparatively high spring bias. As such, the first valve can only be opened by releasing the squeeze bag from a compressed state, and the second valve only by again squeezing the bag. In other words, the subject's spontaneous inspiratory efforts are incapable of operating the valves. This situation is exacerbated by the presence of the mask expiration port that is in direct fluid communication with the atmosphere which assures that insufficient negative inspiratory pressure can be developed in the mask to effect valve actuation.

Further, the advent of the oxygen accumulator squeeze bag resuscitator did not satisfy the need for being able to administer substantially pure oxygen to patients under certain relatively frequently occurring high oxygen demand circumstances, such as resuscitation responsive to cardiac distress or like conditions. The invention disclosed in U.S. Pat. No. 3,796,216, however, represented an early attempt to administer essentially pure oxygen to a subject using a squeeze bag resuscitator. The apparatus disclosed therein included a body member, a squeeze bag, an oxygen inlet, a flapper valve and a face mask. The body member comprises a tubular portion to which the mouth of the squeeze bag is connected. The face mask is joined to the tubular member generally opposite the squeeze bag and an inlet adapted to be connected to a source of breathing gas such as oxygen is provided in the tubular member between the squeeze bag and the face mask. The flapper valve regulates passage of oxygen from the squeeze bag to the face mask.

Unlike those discussed above, the squeeze bag disclosed in U.S. Pat. No. 3,796,216 is not self-restoring but merely flexible or pliable and is continuously inflated with oxygen via the oxygen inlet. When the bag is sufficiently inflated and it is desired to administer oxygen to the subject, the user squeezes the bag to increase the pressure in the tubular member to a level sufficient to cause the flapper valve to expose a mask inhalation port and cover a mask exhalation port whereby the oxygen is passed into the mask for consumption by the subject. Once the contents of the bag have been depleted via squeezing to an extent that the pressure in the body member is insufficient to overcome the bias of the flapper valve, the valve returns to its normal position covering the inhalation port and exposing the exhalation port. At this time, the subject exhales, his expiratory gases passing through the exhalation port, and the bag reinflates. This process is repeated as necessary to facilitate or restore the patients normal breathing pattern.

A functional weakness of this sort of resuscitator is that it is incapable of dispensing pressurized atmospheric air in the event of failure or exhaustion of the pressurized oxygen supply. Specifically, even if the gas source were disconnected from the gas inlet thereby exposing the inlet to the atmosphere, the squeeze bag is not self-restoring. Hence, it cannot create either the negative pressure required to draw air into the inlet or the positive pressure to expel the air therefrom.

U.S. Pat. Nos. 2,399,643, 2,834,339, 3,196,866, 3,316,903, 3,473,529, 4,037,595, 4,077,404, 4,088,131 and 4,121,580 describe self-distending squeeze bag or similar resuscitators variously capable of administering air, oxygen or a mixtures thereof upon compression of the squeeze bag. Pursuant to each of these disclosures, gas flow to and from the subject is effected by the opening and closing of at least one, and usually two or more, spring-biased check valves, flap valves or combinations thereof. In perhaps the simplest of these constructions, i.e., the resuscitators proposed in U.S. Pat. Nos. 3,196,866 and 3,316,903, during expansion of the squeeze bag the oxygen being supplied to the bag will always be mixed with atmospheric air because the resuscitator valve assembly includes ports in communication with the atmosphere and the interior of the bag, which ports are normally open and can only be closed by squeezing the bag. Thus, these resuscitators may together be envisioned as another form of the "oxygen accumulator" type resuscitators previously discussed. And, as noted, resuscitators of this sort are incapable of delivering pure oxygen which may at times be vital depending upon the resuscitation requirements of the subject.

Most of the other resuscitators provided in U.S. Pat. Nos. 2,399,643, 2,834,339, 3,473,529, 4,037,595, 4,077,404, 4,088,131 and 4,121,580 may effectively administer virtually pure oxygen. Nonetheless, their valve assemblies are particularly complex in construction and heavily dependent upon the spring biases of their numerous valves to effect proper resuscitator operation. As such, should the oxygen supply of such a resuscitator be momentarily interrupted, the subject would have to expand considerable inspiratory effort to draw atmospheric air into the resuscitator to satisfy his respiratory requirements. In many instances, the subject may be incapable of such exertion, thereby further aggravating his respiratory distress.

The foregoing demonstrates that pressurized oxygen cannot easily be continuously introduced into a squeeze bag resuscitator without compromising the other functions and essential characteristics of the resuscitator. In efforts to avoid these problems, assorted valving arrangements have been developed for introducing and interrupting the supply of pressurized oxygen into various parts of the resuscitator system. Such valving arrangements are intended to respond automatically to particular conditions or operating states of the resuscitator system, typically function in response to sensings of differential pressures, and are commonly referred to as "demand oxygen supply valves".

Despite their general efficacy, the demand oxygen supply valves heretofore proposed have been unduly complicated in design and operation, costly to manufacture and, because of their numerous parts, susceptible to malfunctioning. One of these valves, that disclosed in U.S. Pat. No. 4,374,521, functions in such manner whereby the pressure of the delivered oxygen impinges upon a flexible flap seal urging the seal into covering relation with ports that communicate with the atmosphere. In the event the flow of oxygen ceases, oxygen pressure is removed from the flap seal and the subject may inspire atmospheric air essentially without resistance. The primary disadvantage of this valve, however, is its sheer complexity. No less than four internal pressure chambers and two biased membrane-type valve elements must work in concert to achieve the desired gas delivery results. Should any of these intricately interrelated components fail to function precisely as designed, oxygen administration will be detrimentally affected, if not totally interrupted.

The assignee of the present invention, Respironics, Inc. of Murrysville, Pa., has developed a simplified squeeze bag resuscitator, discussed at greater length hereinafter, which permits the subject to consume essentially pure oxygen. The oxygen is delivered to a manifold that is in fluid communication with an oxygen reservoir bag, a first flapper valve and a second flapper valve. The first flapper valve regulates gas flow into the squeeze bag and the second flapper valve regulates ambient air flow into the manifold. Under normal operating conditions, the oxygen initially fills the reservoir bag and, if the squeeze bag is in a restoring phase, oxygen flows past the first flapper valve and into the squeeze bag. Alternatively, if the bag is fully restored and the subject inhales, the oxygen may pass the first flapper valve and flow directly to the subject.

Should the oxygen flow be interrupted for any reason, the subject would have ready access to the atmosphere by simply inhaling, thereby drawing the air through the second flapper valve and then the first flapper valve. To assure that ambient air does not mix with the oxygen under normal operation, the spring bias of the second flapper valve has been intentionally designed to be rather significant. Because of this built-in bias, however, the subject may experience considerable resistance when it becomes necessary to breathe air directly from the atmosphere. For reasons mentioned above, the subject may not be able to summon the strength to overcome the bias of the second flapper valve and, consequently, the presence of the resuscitator may hinder rather than promote restoration of his normal respiratory activity.

An advantage exists, therefore, for a squeeze bag type resuscitator including an uncomplicated, substantially bias-free valve means capable of delivering essentially pure oxygen during normal operation while affording a subject unhindered access to atmospheric air in the event of interruption of the oxygen flow.

Apart from the aforementioned deficiencies arising from the construction and/or function of their valve assemblies, optimal performance, versatility and operational convenience of conventional squeeze bag type resuscitator apparatus are encumbered by a number of other component-specific design limitations.

Early forms of resuscitator apparatus commonly included a bellows with a handle at one end thereof, at least one valve for introducing ambient air or other breathing gas into the bellows and a breathing mask at the opposite end of the bellows through which the breathing gas could be pumped into the subject's airway by compressing the bag. To use such an apparatus, an operator would place the breathing mask over the subject's face, grasp the handle and compress and decompress the bellows at appropriate intervals and rates by pushing the handle toward and pulling the handle away from the user's face. Examples of such bellows type resuscitators may be found in U.S. Pat. Nos. Re. 24,193, 2,399,643 and 3,316,903. The structure and function of these apparatus, while generally effective for their intended purposes, nevertheless suffered from several detractions.

First, because the entirety of the resuscitator was positioned directly in front of the subject's face during operation, the apparatus tended to obscure the operator's view of the subject's facial activity which is essential for ascertaining how the subject is responding to the therapy.

Second, the bellows compression force is applied directly toward the subject's face thereby creating percussive effect that is manifestly uncomfortable to the subject. Conversely, by pulling the handle away from the subject's face to expand the bellows, the operator must be cognizant to maintain continued and substantial downward manual force on the mask otherwise the mask will become separated from the subject's face. Obviously, this continuous application of force may also contribute to the subject's discomfort.

The introduction of the squeeze bag style resuscitator (and later versions of bellows type resuscitators) brought forth the notion of connecting the mask to a generally L-shaped tubular member which, in turn, was connected to the squeeze bag or bellows. This seemingly simple but significant development, which is reflected in U.S. Pat. Nos. 3,009,459, 3,262,446, 3,473,529, 4,037,595, 4,077,404, 4,374,521, 4,774,941, 4,821,713, 4,919,132, 5,067,487, 5,109,840 5,140,982 and 5,279,289, effectively alleviated the aforesaid disadvantages of vision obstruction and patient discomfort prevalent in the earlier bellows resuscitators because the bulk of the resuscitator apparatus was disposed laterally away from the subject's face. Even these apparatus, however, were somewhat constrained in application. Specifically, because the L-shaped tubular member is typically a rigid link between the mask and the bellows, the operator must exercise considerable care to assure that the mask does not become separated from the subject's face by shifting of the bellows or squeeze bag. In other words, there is a very limited range of spatial orientations within which the resuscitator may be positioned to productively administer breathing gas.

Greater applicational flexibility was achieved in the squeeze bag resuscitators disclosed in U.S. Pat. Nos. 2,834, 339, 3,196,866, 3,291,121 and 4,501,271 which incorporated flexible conduit between the squeeze bag and the subject interface. These constructions thus permit the squeeze bag to be operated in virtually any orientation. However, the use of flexible conduit is not without disadvantages. That is to say, precisely because of its flexibility, such conduit is prone to folding or kinking. Hence, should the conduit become sufficiently occluded during operation, gas flow to the patient may be interrupted.

To overcome the problem of kinking in respiratory gas delivery conduits, U.S. Pat. Nos. 3,858,615, 3,908,704, 4,000,341 and 4,852,564 have proposed the use of kink-resistant flexible hose. Even these hoses, however, possess certain limitations. More particularly, although less susceptible to kinking than standard flexible conduit, hoses of this sort have a minimum bending radius below which even they will begin to kink. Thus, regardless of the respiratory apparatus with which they are used, such hoses must be of sufficient length to assure that the minimum bending radius threshold will not be crossed, even under the most adverse operating conditions. As a consequence, more hose than would otherwise be desirable must be provided to prevent such an occurrence. The aforementioned squeeze bag resuscitator developed by assignee Respironics, Inc. employs such a kink-resistant hose between its squeeze bag and mask. However, the relatively long flexible hose connecting the squeeze bag to the breathing mask renders the resuscitator somewhat more unwieldy than would be desirable in certain situations where space to maneuver the apparatus is limited.

A further advantage exists, therefore, for a short, kink-resistant flexible tubular member for fluidly connecting a squeeze bag, bellows or similar resuscitator component to a breathing mask or similar patient interface means.

In developing the present invention, it was recognized that the versatility of a resuscitator could be enhanced if the junctures of one or more of its primary fluid delivery components could be constructed so as to permit relative rotation between those components.

When designing a leak-free, rotatable fluid seal, one must balance the competing objectives of minimizing rotational torque and maximizing gas leak resistance. As a consequence, improved rotatability typically comes at the expense of decreased leak resistance, and vice versa. It is known, as exemplified by U.S. Pat. Nos. 4,852,563, 4,938,209 and 5,062,420, to provide rotatable seals between various breathing circuit components of respiratory apparatus. In each of these assemblies, however, there exists considerable areas of surface contact between the mating parts. And, since no gaskets or other sealing material is disclosed as being interposed between these parts, the desired sealing effect appears to be created by maintaining a tight friction fit between the parts. Assuming these seals to be leak-free, therefore, the close tolerances between the parts necessarily detrimentally impacts upon their ability to rotate relative to one another. Conversely, if the parts do permit relatively free rotation, then considerable gas leak is unavoidable (again because of the absence of sealing material).

The aforesaid Respironics, Inc. squeeze bag resuscitator includes a generally freely rotatable sealed connection between its flexible hose (discussed above) and a non-rebreathing valve situated between the flexible hose and the breathing mask. This mutually beneficial result was achieved by providing generous part tolerances and a quantity of silicon-based sealing lubricant between the parts. Although beneficial rotation and sealing characteristics are realized using such an approach, the use of silicon material or other conventional lubricants as the sealing/lubricating means adds to the cost of the system and may introduce potentially physically harmful agents into the breathing circuit.

A further advantage exists, therefore, for a resuscitator having a low-torque, low-leak, environmentally-safe swivel seal at the juncture of one or more of its primary fluid delivery components.

In addition to its squeeze bag, the previously discussed Respironics, Inc. resuscitator also includes an oxygen reservoir bag upstream of the squeeze bag which stores a selected volume of pressurized oxygen prior to its introduction into the squeeze bag. The oxygen bag is preferably formed of thin, pliable plastic (e.g., polyethylene film) which, unlike the squeeze bag, is not self-inflating. The oxygen reservoir bag is generally oblate in shape and open at its opposite ends whereat it is taped or otherwise adhesively and sealingly secured to upper and lower manifolds. The manifolds are respectively connected to the non-rebreathing valve and the squeeze bag and are attached to opposite ends of the flexible hose whereby fluid communication is established between the manifolds by virtue of the flexible hose. So constructed, the oxygen reservoir bag establishes a sealed oxygen chamber about the flexible hose and between the manifolds. A disadvantage of this arrangement is that the additional materials (e.g., tape or adhesive) and attendant labor required to adhesively secure the opposite ends of the oxygen reservoir bag to the manifolds undesirably contribute to the manufacturing cost of the resuscitator. Moreover, if care is not taken in the attachment of the oxygen reservoir bag to the manifolds, oxygen may leak from the system.

U.S. Pat. Nos. 4,917,081 and 4,919,132 teach pliable breathing gas storage bags connected at their opposite ends to components of respiratory apparatus. The bag in U.S. Pat. No. 4,917,081 requires supplemental attachment means to assure its sealing connection. The bag in U.S. Pat. No. 4,919,132 merely receives smooth tubular inserts having no structure to which the bag may positively and sealingly engage to prevent gas leakage from the bag.

In connection with a resuscitator of the type having an oxygen reservoir bag, an advantage exists, therefore, for an improved system by which the oxygen reservoir bag may be sealingly attached to the resuscitator without resort to adhesive tape or other superfluous fastening means.

U.S. Pat. No. 4,501,271 exemplifies a conventional, fully disposable resuscitator. Such apparatus is designed for one-time use and effectively prevents cross-contamination. Disadvantageously, however, fully disposable resuscitators must be discarded in their entirety after a single use. Thus, their disposal is expensive and they are costly to maintain as inventory. Further, because many of the resuscitator components are subject to patient contamination, and also because they are not sterilized after usage, resuscitators of this type are not considered to be especially environmentally compatible.

Fully reusable resuscitators, such as that described in U.S. Pat. No. 2,834,339, for example, are sterilizable and capable of multiple usages. While seemingly more economically desirable, these resuscitators require sterilization after each use. As such, considerable handling, disassembly, assembly and testing is needed to assure that the apparatus is not only properly sterilized but that it also functions properly after sterilization. The diseconomies associated with such practice are manifest.

U.S. Pat. Nos. Re. 24,193, 2,834,339, 3,196,866, 3,473, 529 and 4,374,521 represent examples of squeeze bag resuscitators whose squeeze bags are self-sealingly or "stretch-fit" onto the remainder of the apparatus. None of these disclosures, however, address the economic, environmental and safety advantages that may be achieved through development of a partially reusable resuscitator, particularly one whose squeeze bag may be repeatedly sterilized and reused and whose other components may be discarded after each use.

A further advantage exists, therefore, for a squeeze bag resuscitator that permits ready sterilization and reuse of its most rugged, costly and yet most easily sterilized component, i.e., its squeeze bag, and which simultaneously affords convenient discardability of its other functional components as an integrated disposable assembly.

SUMMARY OF THE INVENTION

In accordance with the present invention, there is provided a squeeze bag type resuscitator apparatus including several novel component features which individually and collectively enhance apparatus performance and durability while simultaneously producing an apparatus that is uncomplicated in design, easy to manufacture and low in cost.

Generally, the resuscitator apparatus comprises a resilient, self-inflating squeeze bag having a single combined inlet/outlet which is preferably removably connected to a first manifold in operative communication with a substantially unbiased valve means. The first manifold includes an inlet coupling adapted for connection to a source of pressurized respiratory gas such as oxygen and an outlet coupling adapted for connection to a first end of a tubular connector. The tubular connector is desirably formed as a short, kink-resistant, flexible hinge member. The second end of the tubular connector is adapted for connection to an inlet coupling of a second manifold in operative communication with a conventional patient valve, such as, for example, a non-rebreathing valve contained within a tubular, preferably L-shaped housing. The tubular housing includes a first leg connected to the second manifold and a second leg extending substantially perpendicular to the first leg, the second leg being adapted for connection to a subject interface member such as a breathing mask or the like.

An oxygen reservoir bag preferably formed of thin, pliable plastic surrounds the tubular connector and is sealingly attached at first and second ends thereof to the first and second manifolds, respectively. According to a preferred embodiment, the ends of the oxygen reservoir bag are attached to the manifolds without supplemental fastening means such as adhesives.

When it is desired to administer oxygen to a subject, a pressurized oxygen source is connected via suitable means such as flexible hose to the inlet coupling of the first manifold. The inlet coupling is fluidly coupled to first interior passageways provided in the first manifold, which passageways communicate with the interior of the oxygen reservoir bag. Hence, by flowing through the inlet coupling and the first interior manifold passageways, the oxygen serves to inflate the oxygen reservoir bag. The first interior passageways simultaneously deliver the pressurized oxygen to a chamber within the first manifold which is in regulated communication with the ambient atmosphere by virtue of a first valve element of the substantially unbiased valve means. Concurrently, oxygen is transmitted through second interior manifold passageways which fluidly link the interior of the oxygen reservoir bag with the interior of the squeeze bag; a second valve element of the substantially unbiased valve means functions to regulate this flow.

In accordance with the present invention, the bias of at least the first valve element of the valve means and, preferably, the biases of both the first and second valve elements, should be negligible. In the preferred form, the valve means is a unitary, thin, flexible flap, the first valve element constituting a first portion of the flap and the second valve element a second portion thereof. Fabricated as such, the oxygen pressure within the first interior manifold passageways is likewise produced in the manifold chamber, which pressure impinges upon the first valve element causing same to close ambient air inlet port means formed in the first manifold, thereby precluding atmospheric air from passing to the subject during oxygen administration. At the same time, a fraction of the pressurized oxygen flows through the second interior manifold passageways past the second valve element and into the interior of the squeeze bag.

At this stage, the breathing mask may be placed in sealing engagement with the subject's face covering his mouth and nose, whereby resuscitation may begin. The operator then squeezes the squeeze bag which urges the second valve element to cover and seal the second interior manifold passageways. This action simultaneously ceases oxygen flow into the squeeze bag and expels the gaseous contents thereof sequentially through the first manifold outlet coupling, the flexible tubular hinge member, the second manifold inlet coupling, the non-rebreathing valve, the tubular housing and the breathing mask whereby it may be consumed by the subject. Thereafter, the operator relaxes the squeezing force applied the squeeze bag thus permitting it to restore itself to its normal shape. This self-distension of the squeeze bag creates negative pressure within the squeeze bag which causes the second valve member to widely open whereby oxygen within the oxygen reservoir bag is drawn through the second interior manifold passageways and into the squeeze bag. During this time, the subject may exhale whereupon his expiratory gas passes through the non-rebreathing valve to the atmosphere in the manner known in the art.

The volume of the oxygen reservoir bag is desirably greater than the difference in volume of the squeeze bag between its compressed and restored states. Hence, upon self-restoration of the squeeze bag, residual pressure within the oxygen reservoir bag (assisted in part by the continuous introduction of oxygen through the first manifold inlet) is likewise applied in the first manifold chamber at a level sufficient to cause the first valve element to remain in covering and sealing relation with the ambient air inlet port means. Consequently, no atmospheric air is permitted to enter the resuscitator during an oxygen administration procedure, whereby the subject receives the full therapeutic benefits of pure oxygen resuscitation.

Continuing, with the squeeze bag restored (during which time the oxygen reservoir bag begins to reinflate with oxygen), the operator may then squeeze the squeeze bag, thereby closing the second valve element and delivering the oxygen to the subject in the manner described above. The subject may exhale while the user permits the squeeze bag to reinflate and the process may be repeated as circumstances dictate.

In the event the oxygen supply should falter, the substantially unbiased valve means of the present invention would permit the subject immediate and unrestricted access to atmospheric air. That is, because the first and second valve elements are substantially unbiased, they do not naturally tend to sealingly engage with, respectively, the ambient air inlet port means and the second interior manifold passageways. As a result, the subject may inhale ambient air essentially without resistance to air flow. Specifically, upon inhalation, atmospheric air may enter the ambient air inlet port means, flow around the first valve element, through the manifold chamber and first and second interior manifold passageways, past the second valve element, and, thereafter, through the flexible tubular hinge member, second manifold, non-rebreathing valve, tubular housing and breathing mask. The principle resistance to air flow under these conditions would be that associated with the inspiratory valve element of the non-rebreathing valve, which resistance in most instances is minimal.

As previously mentioned, the invention further comprises a novel flexible tubular hinge member that fluidly connects the first and second manifolds. Among the advantages to the construction of the flexible hinge member are that it is of short length (in fact, less than half the length of its counterpart flexible hose employed for similar purposes in the aforementioned Respironics, Inc. resuscitator), it permits approximately 180° of flexure between the squeeze bag and the nose mask in any plane, and is completely kink-resistant. As such, the flexible tubular hinge member affords a more compact and, therefore, more convenient resuscitator apparatus than heretofore known in the art which also effectively prevents occlusion of gas flow to the subject.

The tubular hinge also cooperates with the inlet coupling of the second manifold to effect a low-torque, low-leak, environmentally-safe swivel seal which further enhances the positionability of the breathing mask relative to the squeeze bag to facilitate resuscitation of the subject by the user.

Lastly, the invention additionally contemplates a self-sealing oxygen reservoir bag which sealingly attaches to the first and second manifolds without need of adhesive tape or other fastening means.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments therefor shown, by way of example only, in the accompanying drawings, wherein.

DETAILED DESCRIPTION OF THE INVENTION

In terms of disposability, manually operated "squeeze bag" type resuscitator apparatus have generally evolved along two product lines: those which are totally disposable and, at the opposite extreme, those which are completely reusable.

Fully disposable resuscitators, an example of which is provided in U.S. Pat. No. 4,501,271, are typically simple to operate, do not cause cross-contamination, and are ready to use when removed from their packaging. These apparatus are designed for one-time use and must be discarded in their entirety after such usage. To their detriment, however, resuscitators of this sort are costly to maintain as inventory, commensurately expensive to dispose, and not regarded as environmentally sound.

Reusable resuscitators, on the other hand (such as that disclosed in U.S. Pat. No. 2,834,339), would appear to be a more attractive alternative from an economic perspective because of the capacity of these devices to be repeatedly used. Nevertheless, these products typically require extensive handling, disassembly, assembly, testing and disinfection and/or sterilization, which factors possess inherent monetary and labor costs and which, if not properly executed, result in apparatus malfunction and/or contamination.

The present invention seeks to combine the best attributes of disposable and reusable resuscitators while realizing a product of low cost and high reliability. To those ends, there is proposed a resuscitator whose primary functional components apart from the squeeze bag (e.g., manifolds, valves, oxygen reservoir, PEEP adjustment mechanisms, etc.) are preferably, but not necessarily, incorporated into a common disposable assembly which is detachably connectable to a reusable and disinfectable and/or sterilizable squeeze bag. The disposable assembly includes several novel components of uncomplicated design and operation which enhance convenience, apparatus performance and patient comfort. Further, the squeeze bag attachment design is such that it requires no tools for assembly and may be easily performed by any hospital technician or other health care worker.

Figure 1:
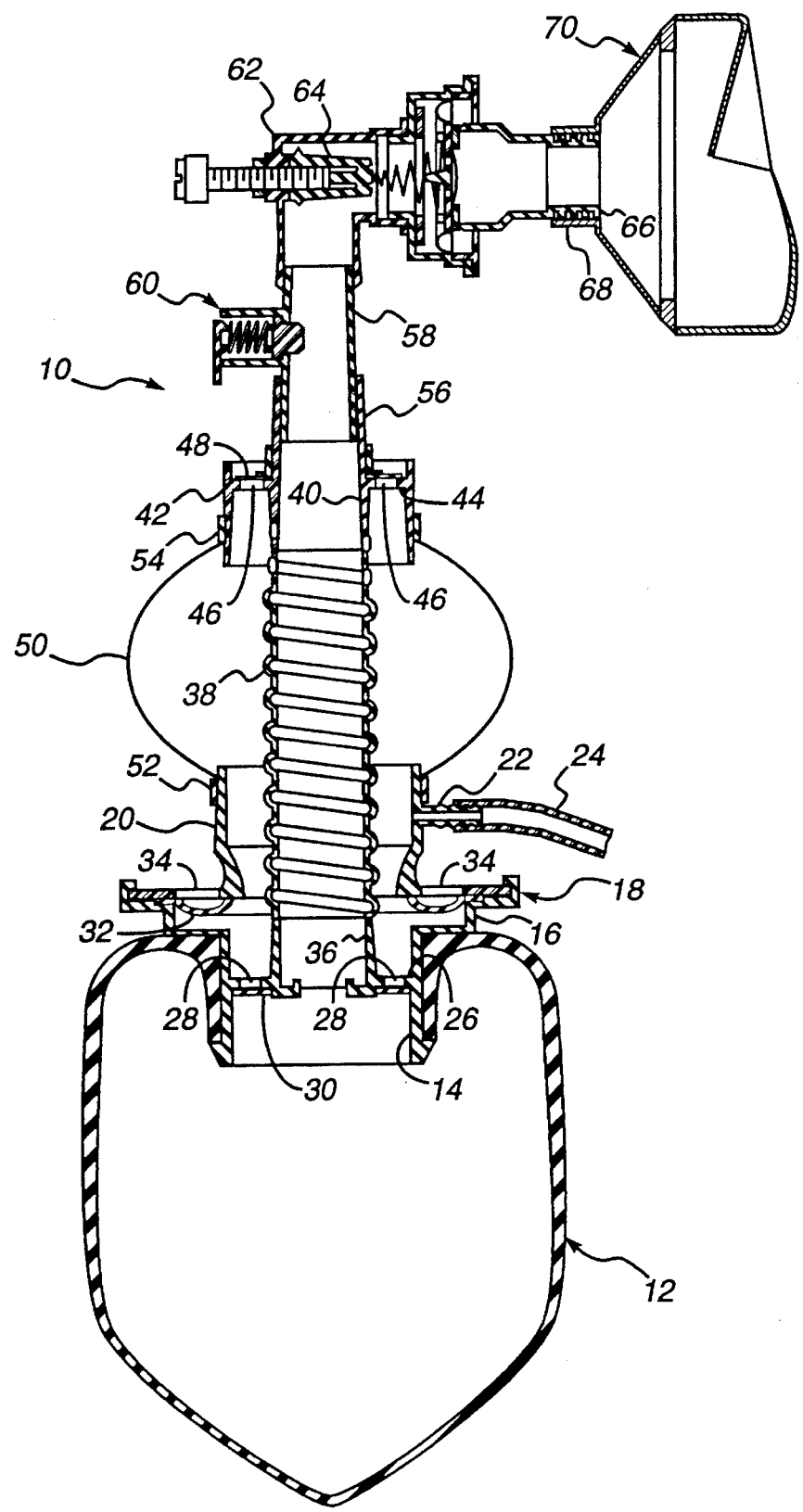
FIG. 1 is an elevational cross-section view of a presently known, fully disposable squeeze bag resuscitator apparatus.

The instant invention traces its lineage most closely to the squeeze bag resuscitator apparatus 10 illustrated in FIG. 1. Apparatus 10 represents a fully disposable device which is manufactured by Respironics, Inc. of Murrysville, Pa. under the trade name BagEasy®. Apparatus 10 includes a squeeze bag 12 of resilient, self-restoring material such as rubber, neoprene, flexible PVC or the like, having a single annular inlet/outlet opening 14 that is sealingly affixed to a lower housing portion 16 of a first manifold 18 by a suitable adhesive such as cyanoacrylate. An upper housing portion 20 of the first manifold is provided with an oxygen inlet coupling 22 to which a gas delivery means such as flexible conduit 24 may be attached so as to deliver pressurized oxygen from a suitable oxygen source (not illustrated) to the interior of the first manifold.

Integral with and projecting radially inwardly of the first manifold housing is an annular wall 26 provided with a plurality of ports 28 through which atmospheric air and/or pressurized oxygen may be introduced into the interior of squeeze bag 12 in a manner to be described in greater detail later herein in connection with the discussion of FIGS. 25 through 28. An annular, resilient, flapper valve 30 fabricated from flexible synthetic resin or rubber is normally biased into a closed position covering the ports 28 and regulates the flow of gas into the squeeze bag. Reference numeral 32 identifies an annular, resilient flapper valve clamped at its outer periphery between the upper and lower housing portions of the first manifold. Flapper valve 32, like valve 30, is also manufactured from flexible material but, rather than having a simple, flat disc-like cross-sectional shape, is instead formed into an arched, substantially semi-toroidal configuration. Valve 32 assumes this configuration specifically to increase its spring bias and, therefore, its resistance to atmospheric air being introduced into the first manifold through ambient air inlet ports 34 provided in the upper manifold housing portion 20 during resuscitation involving oxygen administration. This phenomenon will also be elaborated upon as part of the description of FIGS. 25 through 28.

A tubular outlet coupling 36 is formed integrally with the annular wall 26 and projects therefrom in a direction opposite that of the squeeze bag. Snugly receiving and preferably adhesively affixed to the outer circumference of the outlet coupling 36 is one end of a flexible corrugated hose 38 the opposite end of which is desirably similarly joined to a tubular inlet coupling 40 of a second manifold 42. Coupling 40 is integral with a radially inwardly projecting annular wall 44 of second manifold 42. Annular wall 44 includes a plurality of ports 46 which are normally closed by a thin, flexible, annular flapper valve 48 constructed substantially similar to but having a somewhat lower spring bias than flapper valve 30. A generally oblate, open-ended, oxygen reservoir bag 50 fabricated from thin, pliable plastic is sealingly affixed at its opposite ends by adhesive tape 52 and 54 to the exteriors, respectively, of the first manifold upper housing portion 20 and the second manifold 42. As a consequence of their respective biases, therefore, when the oxygen reservoir bag 50 is fully inflated (as depicted in FIG. 1), and as oxygen continues to flow into the bag through flexible conduit 24 and first manifold inlet coupling 22, flapper valve 48 yields more easily than flapper valve 30 whereby oxygen overflow is vented through ports 46 to the atmosphere rather than through ports 28 to the interior of the squeeze bag.

Projecting from the side of the annular wall 44 opposite the inlet coupling 40 is a tubular outlet coupling 56 that matingly receives one end of a tubular member 58 that may or may not be fitted with a "pop-off" or similar valve device 60 operable to relieve excess system pressure. The other end of tubular member 58 is joined to the first leg of a generally L-shaped tubular non-rebreathing valve housing 62 which preferably contains therewithin an adjustable PEEP non-rebreathing valve assembly, generally indicated at 64, of any conventional structure and function known to those in the art. The second leg of housing 62 extends substantially perpendicularly to the first leg thereof and is fitted with an outlet 66 adapted to be frictionally and rotatably received within an inlet 68 of a conventional respiratory mask 70.

Figure 2:
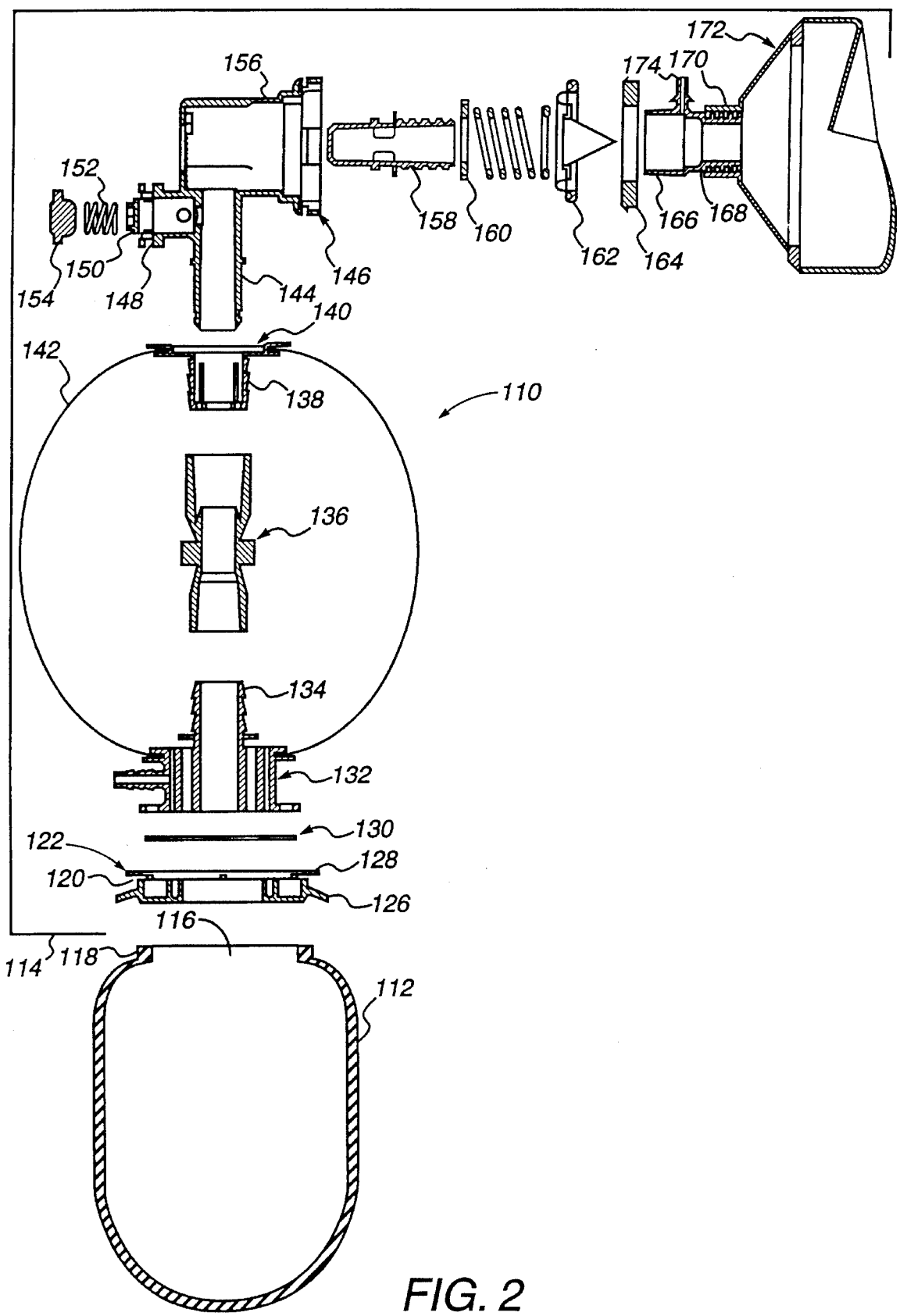
FIG. 2 is an exploded, elevational cross-section view of the squeeze bag resuscitator apparatus of the present invention.
Figure 3:
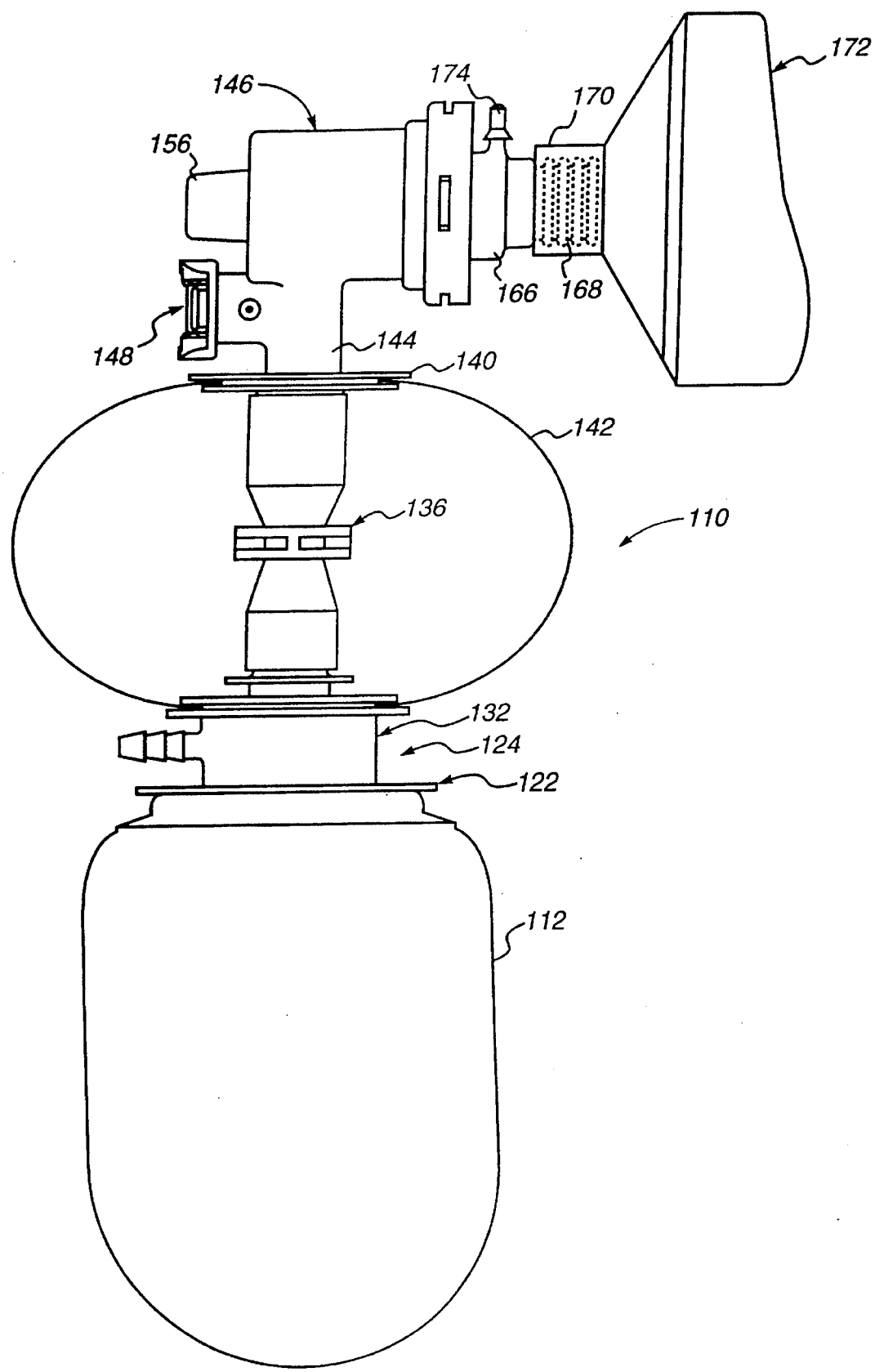
FIG. 3 is an assembled elevational view of the squeeze bag resuscitator apparatus of the present invention.

Referring to FIGS. 2 and 3, there is shown a squeeze bag resuscitation apparatus constructed in accordance with the present invention and identified generally by reference numeral 110. FIG. 2, in particular, generally reveals the essential components of the invention (many of which are more fully developed in subsequent drawing figures), as well as preferred forms of other nonessential but beneficial components that may be deployed in connection therewith.

As mentioned previously, it is contemplated that all functional components apart from squeeze bag 112, i.e., all elements embraced by bracket 114 in FIG. 2, be preferably, but not necessarily, incorporated into a single disposable assembly. As such, the sole reusable component would be the squeeze bag 112. The squeeze bag may be formed of any compressible, resilient, self-restoring, disinfectable and/or sterilizable material such as rubber, neoprene, flexible PVC, or the like, with a presently preferred material being molded and fully autoclavable silicon rubber.

Figure 22:
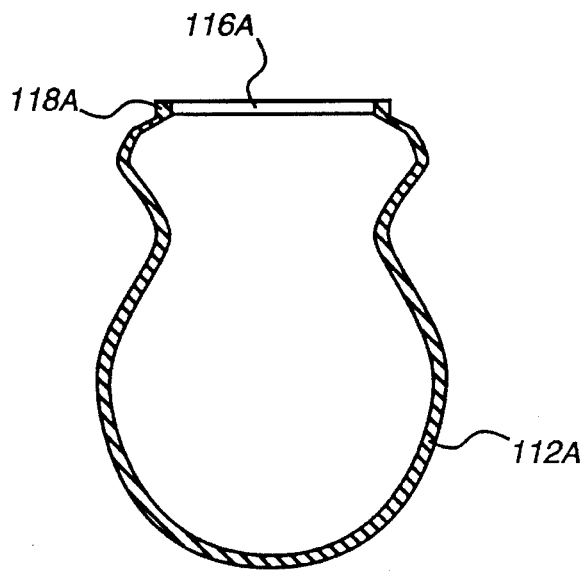
FIG. 22 is an elevational cross-section view of a preferred embodiment of a squeeze bag adapted for use with the squeeze bag resuscitator apparatus of the present invention.
Figure 23:
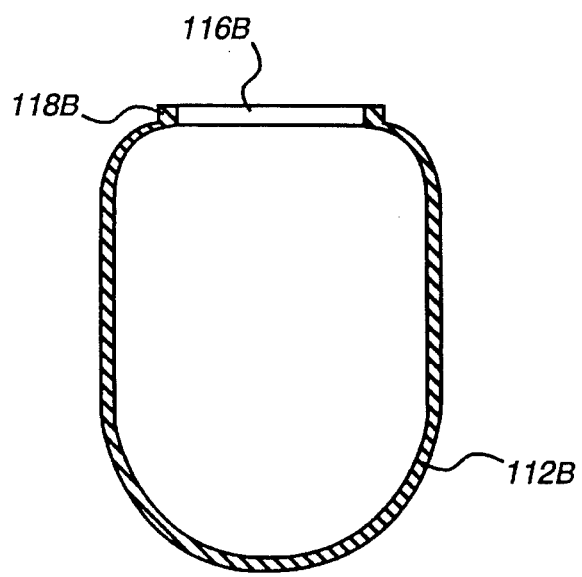
FIG. 23 is an elevational cross-section view of a further preferred embodiment of a squeeze bag adapted for use with the squeeze bag resuscitator apparatus of the present invention.
Figure 24:
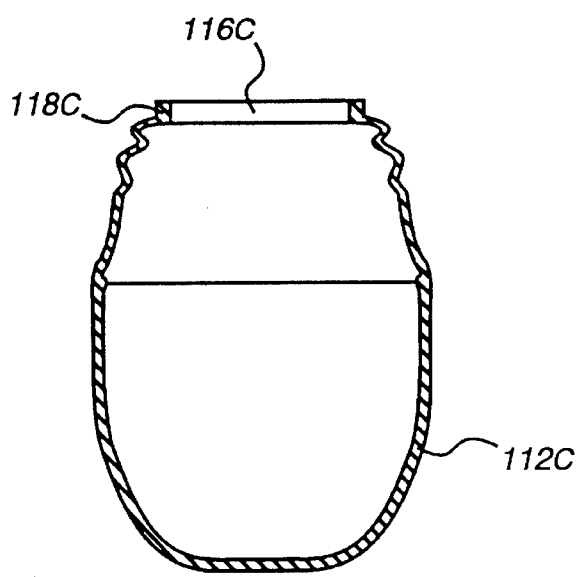
FIG. 24 is an elevational cross-section view of a further preferred embodiment of a squeeze bag adapted for use with the squeeze bag resuscitator apparatus of the present invention.

Squeeze bag 112 (three alternative embodiments of which are shown in FIGS. 22, 23 and 24) includes a single inlet/outlet opening 116 defined by a bead-type collar 118. The collar has a cross-sectional configuration that is adapted to be matingly received in, and has an opening diameter less than, a correspondingly shaped annular engagement groove 120 formed in a lower housing portion 122 of a rigid first manifold 124 (FIG. 2) molded from a suitable synthetic resinous material. To attach the squeeze bag to the first manifold lower housing portion, therefore, the collar 118 must first be manually stretched to enlarge the squeeze bag opening 116 such that it may pass a lower flange 126 of first manifold lower housing portion 122. Once the lower flange has been cleared, the user merely releases the collar 118 whereby it snaps into mating and fluid sealing engagement with groove 120 between lower flange 126 and an upper flange 128.

As will be described at greater length hereinafter, a valve means 130 is positioned between the lower housing portion 122 and an upper housing portion 132 of the first manifold 124. The upper housing portion 132 has an outlet coupling 134 adapted to be frictionally received within one end of a tubular connector 136, the opposite end of which likewise frictionally engages an inlet coupling 138 of a second rigid manifold 140.

A thin, pliable oxygen reservoir bag 142, which is desirably fabricated from non-self-restoring plastic film such as polyurethane, polyethylene or similar material, sealingly engages grooves provided in the second manifold 140 and the upper housing portion 132 of the first manifold 124. This mode of attachment will likewise be further examined hereinafter.

The inlet coupling 138 of the second manifold 140 latchingly engages a first leg 144 of a rigid, generally L-shaped tubular housing 146 which, like the second manifold 140, may be formed from molded synthetic resin. The L-shaped tubular housing may optionally be fitted with a "pop-off" valve 148 or similar relief valve (especially, for example, when the resuscitator apparatus 110 is to be used for resuscitation of infants or children) for venting excess system pressure which may otherwise be inadvertently delivered to the subject undergoing resuscitation. The components of such a relief valve may include a piston 150, spring 152 and toggle 154.

Tubular housing 146 further comprises a second leg 156 extending substantially perpendicularly to first leg 144. Leg 156 is adapted to contain the essential elements of a non-rebreathing valve, preferably an adjustable PEEP valve, the components of which may include, for example, adjustment screw 158, a compression spring 160, a "duck-bill" type non-rebreathing valve element 162 and a retention ring 164. An inhalation/exhalation fitting 166 projects from the second leg 156, which fitting includes an outlet 168 adapted for frictional insertion into and rotatable support within an inlet 170 of a conventional respiratory mask 172 (or other suitable means for providing an interface between the resuscitator apparatus and the airway of a subject including, but not limited to, an intubation tube or nasal prongs) and may, as an option, be provided with a manometer pick-off 174.

Figure 4:
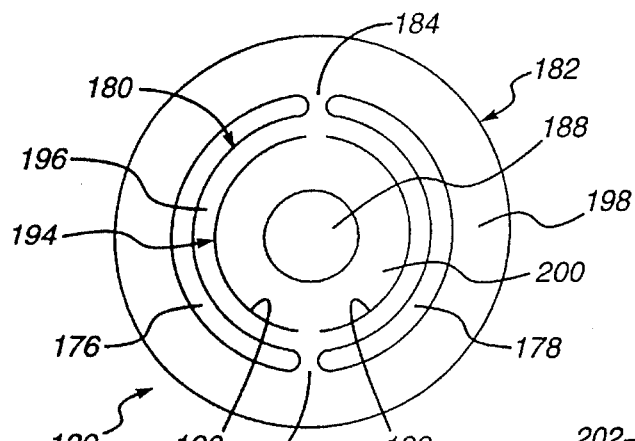
FIG. 4 is a plan view of a preferred embodiment of a substantially unbiased valve means adapted for use with the squeeze bag resuscitator apparatus of the present invention, the valve means being operable to regulate the flow of oxygen and/or air into the squeeze bag during a resuscitation procedure.
Figure 5:
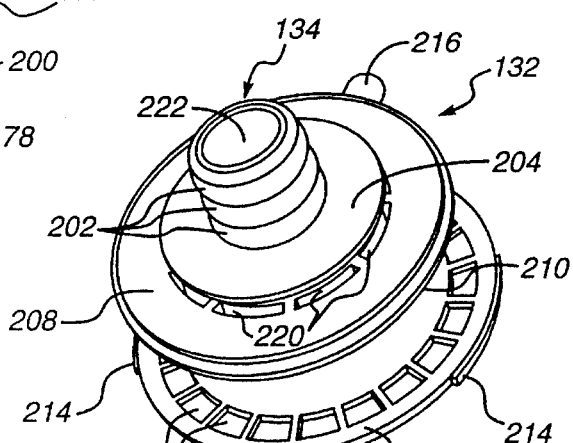
FIG. 5 is a perspective view of a preferred embodiment of an upper housing portion of a first manifold adapted for use with the squeeze bag resuscitator apparatus of the present invention.
Figure 6:
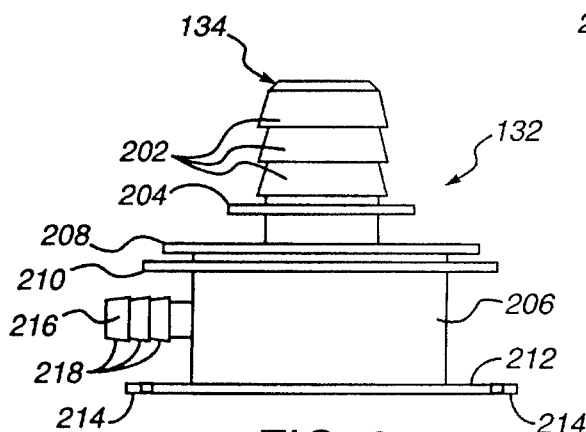
FIG. 6 is an elevational view of the upper housing portion of the first manifold shown in FIG. 5.
Figure 7:
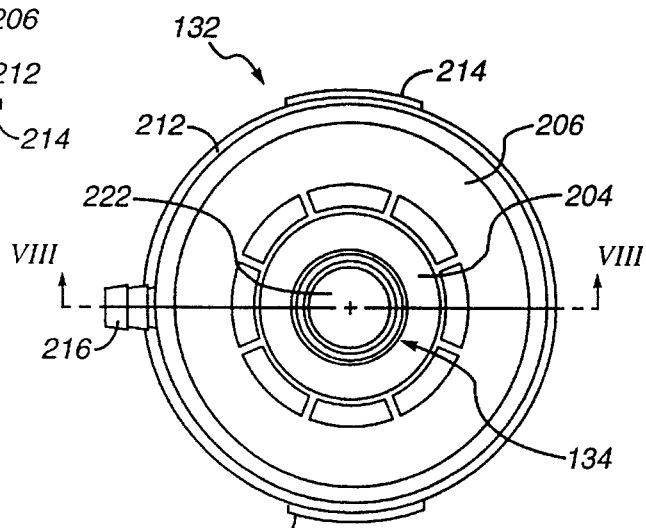
FIG. 7 is a top plan view of the upper housing portion of the first manifold shown in FIG. 5.

FIG. 4 illustrates the details of a presently preferred construction of the valve means 130 for regulating flow of atmospheric air and a pressurized breathing gas such as oxygen through the first manifold 124 and for permitting introduction of pressurized breathing gas and atmospheric air into the squeeze bag 112. Valve means 130 desirably comprises a thin (approximately 0.030 inch), flexible, unitary, die-cut disk of Shore A 50 durometer silicone rubber, although other materials having similar properties and physical characteristics may be suitably employed for this component. A pair of opposed, substantially semicircular openings 176 and 178 effectively divide the valve means 130 into an inner region 180 and a concentrically disposed annular outer region 182 joined by opposed bands of material 184 and 186 separating the ends of the arcuate openings 176 and 178. The inner region 180 includes a central aperture 188 and is further subdivided by opposed, substantially semicircular slits 190 and 192 thereby producing an annular inner region 194 circumscribed by a concentric support ring 196. Suffice it for the moment to say that the annular outer region 182 establishes a first, substantially unbiased, flapper valve element 198 for permitting unrestricted introduction of ambient air into the resuscitator apparatus 110 in the event the oxygen supply should be interrupted whereas annular inner region 194 constitutes a second, substantially unbiased valve element 200 for permitting introduction of either pressurized oxygen or ambient air into the squeeze bag. The functions of these elements as well as those of the semicircular openings 176 and 178, the central opening 188 and the support ring 196 will be more fully appreciated by reference to the descriptions of FIGS. 10, 13 and 29 through 32, infra. Further, although preferably constructed as a unitary component, valve means 130 may, in fact, comprise two or more separate components having the appropriate physical and functional characteristics to effectuate the valving operations of the first and second valve elements 198 and 200.

FIGS. 5 through 10 each depict a presently preferred embodiment of the upper housing portion 132 of the first manifold 124. As mentioned above, upper housing portion 132 includes an outlet coupling 134 adapted to be frictionally received within one end of a later-described flexible tubular hinge member 136 (FIGS. 15, 16, 20 and 21). To augment this frictional engagement, the outlet coupling is preferably provided with at least one or, more preferably, a plurality of outwardly tapering rings 202 about its circumference so as to present an annular barbed engagement surface for gripping the interior of the flexible tubular hinge member. The outlet coupling 134 also preferably carries a radially projecting abutment flange 204 to prevent overextension of the flexible tubular hinge member onto the coupling.

Beneath the outlet coupling 134, the upper housing portion 132 has a substantially cylindrical body 206 bounded at its top by a pair of spaced-apart radially projecting oxygen reservoir bag retaining flanges 208 and 210, and at its bottom by a radially projecting flange 212 having means 214 such as tabs for attaching the upper housing portion 132 of the first manifold 124 to the lower housing portion 122 thereof.

Laterally extending from the cylindrical body 206 of upper housing portion 132 is a tubular inlet coupling 216 to which a gas delivery means such as flexible conduit (not illustrated) may be frictionally attached. To promote secure retention of the flexible conduit, inlet coupling 132 may be provided with one or more outwardly tapering rings 218 similar to rings 202 of outlet coupling 134. The flexible conduit functions to deliver pressurized breathing gas (e.g., oxygen) from a suitable source thereof (also not illustrated) through the inlet coupling to the interior of the upper housing portion of the first manifold.

Figure 8:
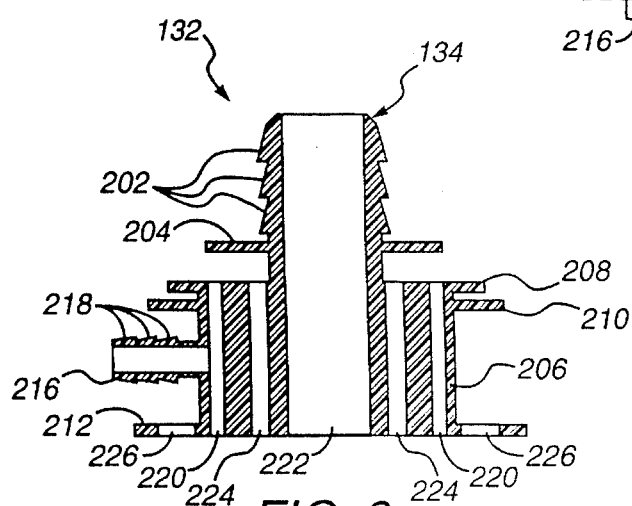
FIG. 8 is an elevational cross-section view of the upper housing portion of the first manifold shown in FIG. 5.
Figure 9:
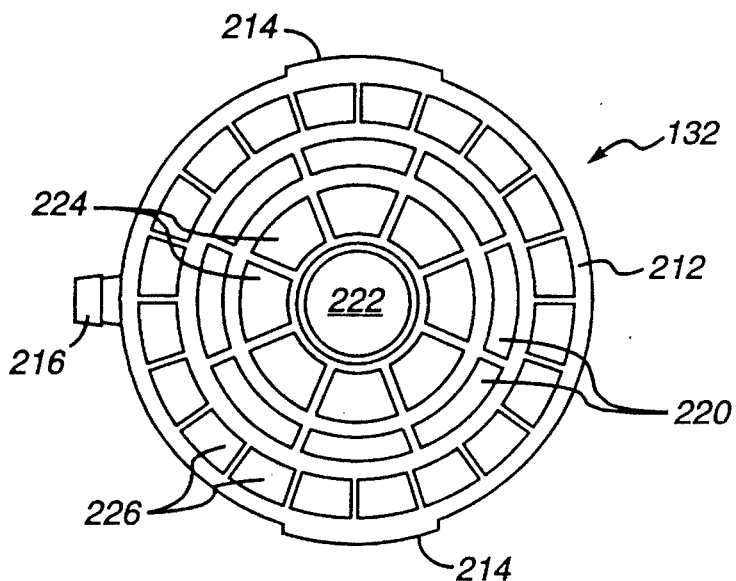
FIG. 9 is a bottom plan view of the upper housing portion of the first manifold shown in FIG. 5.

As perhaps most clearly illustrated in FIGS. 8 and 9, inlet coupling 216 is fluidly coupled to at least one or, preferably, a plurality of first interior passageways 220 extending longitudinally through the cylindrical body 206 between flange 208 and flange 212. First interior passageways 220 are generally arcuate in cross-section and are disposed in a ring-like array about a continuous, open-ended, longitudinally-extending, central bore 222 passing through the entirety of the upper housing portion. Concentrically disposed between central bore 222 and the first interior passageways 220 is at least one or, preferably, a plurality of second interior passageways 224 also extending longitudinally through the cylindrical body 208 between flanges 208 and 212. Like the first interior passageways, the second interior passageways are generally arcuate in cross-section and are arranged in ring-like fashion about the central bore. At least one or, preferably, a plurality of ambient air inlet ports 226 of generally arcuate cross-sectional configuration are provided in the lowermost flange 212 and are concentrically disposed in a ring-like array about the first interior passageways 220.

Figure 10:
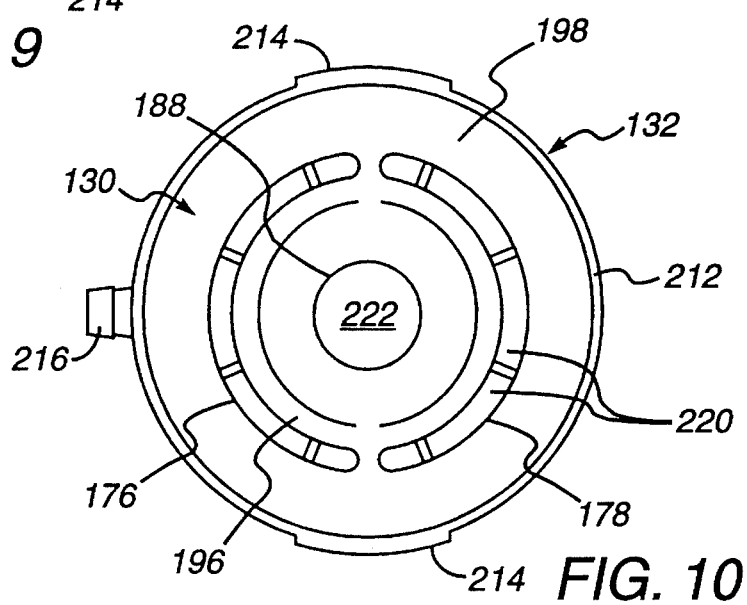
FIG. 10 is a view similar to FIG. 9 with the valve means of FIG. 4 superimposed thereon to illustrate the working disposition of the valve means relative to the upper housing portion of the first manifold.
Figure 11:
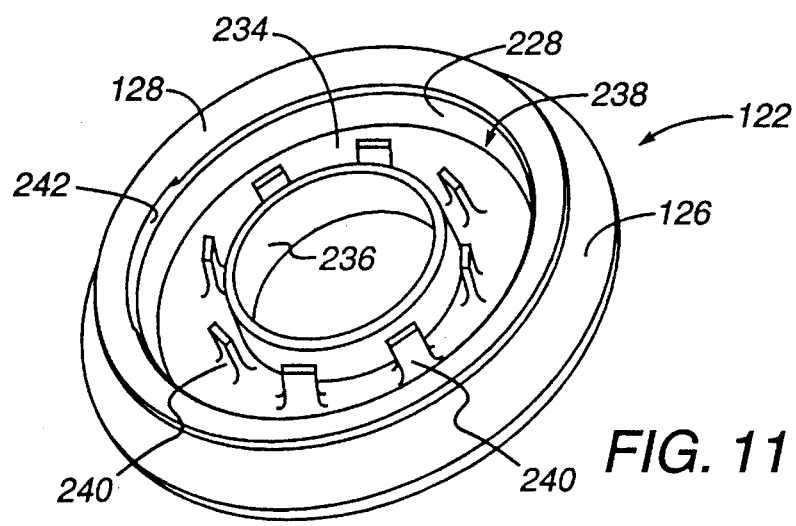
FIG. 11 is a perspective view of a preferred embodiment of a lower housing portion of the first manifold, which lower housing portion additionally serves as an adaptor member to which the squeeze bag may be releasably attached.
Figure 12:
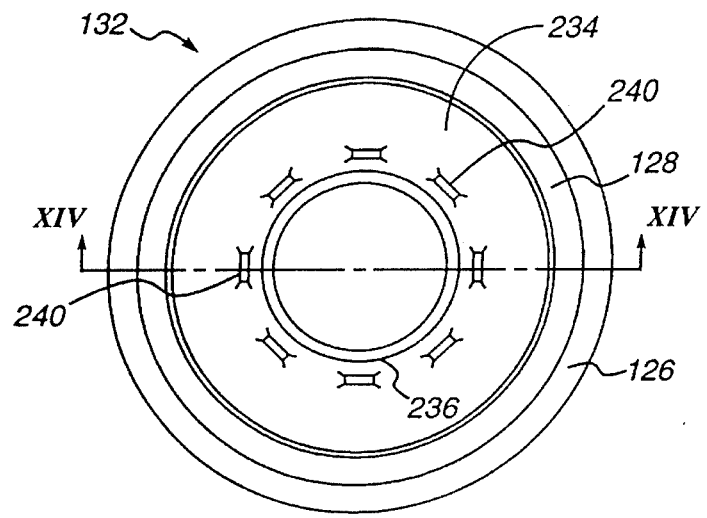
FIG. 12 is a top plan view of the lower housing portion of the first manifold shown in FIG. 11.

FIG. 10 illustrates the working disposition of the valve means 130 relative to the upper housing portion 132. In particular, the valve means is specifically dimensioned such that the semicircular openings 176 and 178 and the central aperture 188 respectively expose the first interior passageways 220 and central bore 222. Conversely, the first substantially unbiased flapper valve element 198 is sized and shaped so as to cover the ambient air inlet ports 226; the second substantially unbiased flapper valve element 200 is adapted to cover the second interior passageways 224; and the support ring 196 is confined to span the circular region between the first and second interior passageways.

The functional interrelationship of the first and second interior passageways and the ambient air inlet ports of the upper housing member vis-a-vis the first and second valve elements of the valve means will be best appreciated from the description of FIGS. 29 through 32, infra.

Figure 13:
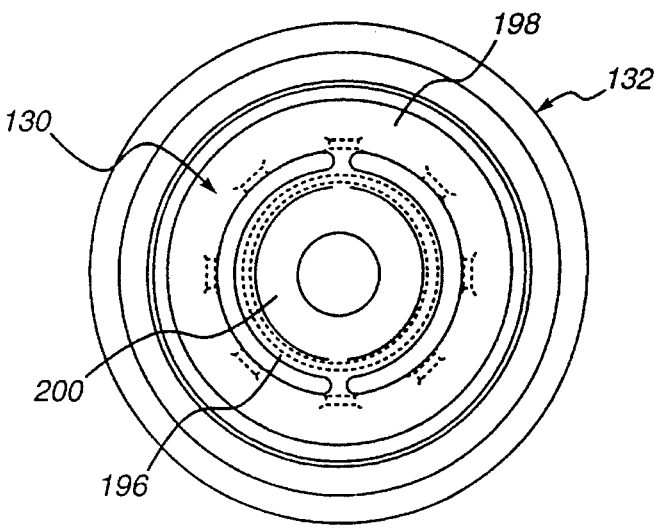
FIG. 13 is a view similar to FIG. 12 with the valve means of FIG. 4 superimposed thereon to illustrate the working disposition of the valve means relative to the lower housing portion of the first manifold.
Figure 14:
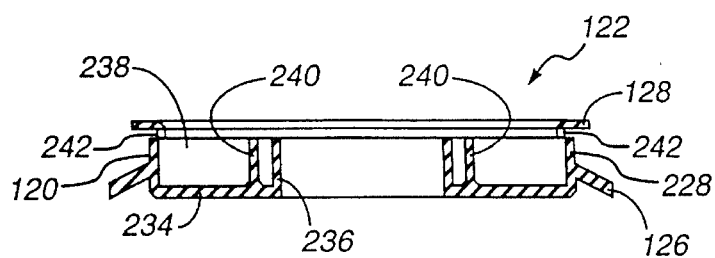
FIG. 14 is an elevational cross-section view of the lower housing portion of the first manifold shown in FIG. 11.

Turning to FIGS. 11 through 14 there is shown a presently preferred embodiment of the lower housing portion 122 of the first manifold 124. Referring initially to FIG. 14, it will be seen that lower housing portion 122 includes a cylindrical body 228 bounded by radially projecting upper flange 128 extending substantially perpendicular to the cylindrical body, and a radially projecting lower flange 126 that slopes in a direction away from the upper flange. The upper flange 128, the cylindrical body 228 and the lower flange 126 define the aforementioned annular engagement groove 120 (FIG. 2) within which the correspondingly shaped collar 118 of the squeeze bag 112 is releasably received.

Contiguous with the cylindrical body 228 is a lower, radially inwardly directed, annular wall 234 that terminates in a truncated inner cylindrical wall 236 spaced from and substantially parallel to the cylindrical body 228. The cylindrical body 228, annular wall 234 and cylindrical wall 236 thus define an annular first manifold chamber 238, the function of which will be discussed hereinafter. Valve support means 240, preferably in the form of a plurality of angularly spaced-apart braces, project upwardly from annular wall 234 between the cylindrical body 228 and the inner cylindrical wall 236. Desirably, the distal ends of the inner cylindrical wall and the support means are coplanar as is shown in FIG. 14. The cylindrical body is also preferably formed with a pair of opposed retention slots 242 adapted to receive tabs 214 of the upper housing portion 132 (FIGS. 5–7 and 10) to thereby enable clamping of the valve means 130 between the upper and lower housing portions of the first manifold 124.

In this regard, FIG. 13 reveals the working disposition of the valve means 130 relative to the lower housing portion 132. The radially innermost edge of the first valve element 198 is discontinuously supported atop the distal ends of the valve support means 240, whereby the outer radial regions of the first valve element are left unsupported. Likewise, the valve means support ring 196 is of generally the same dimensions as, and is adapted to be supported by, the distal end of the inner cylindrical wall 236. As such, the second valve element 200 is not directly supported by any structure of the lower housing portion 132.

Figure 15:
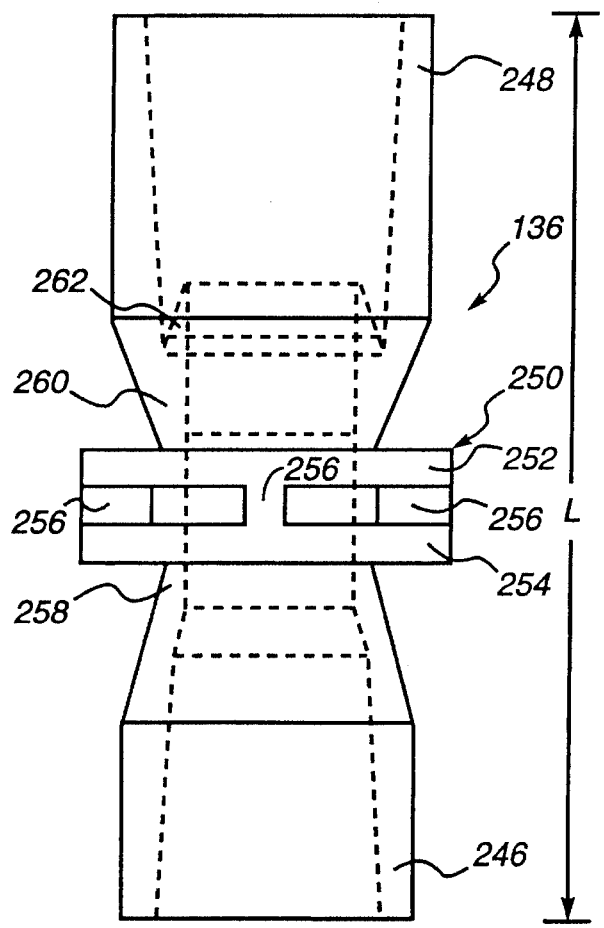
FIG. 15 is an elevational view of a preferred embodiment of a flexible tubular hinge member adapted for use with the squeeze bag resuscitator apparatus of the present invention, specifically for fluidly connecting the aforesaid first manifold with a second manifold.
Figure 16:
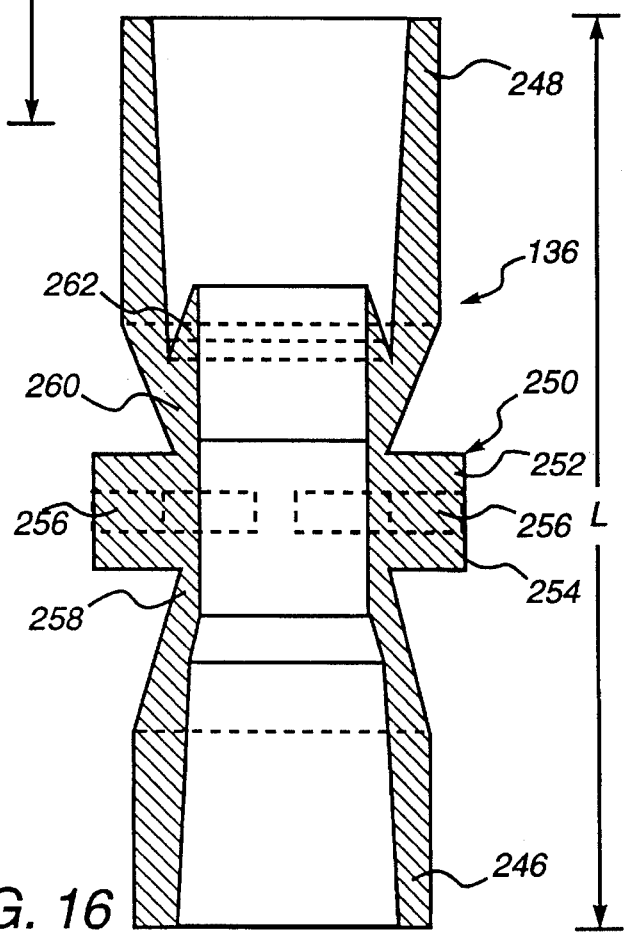
FIG. 16 is an elevational cross-section view of the flexible tubular hinge member of FIG. 15.

FIGS. 15 and 16 represent a presently preferred embodiment of the flexible tubular hinge member 136 for fluidly connecting the first manifold 124 with the second manifold 140 (the details of which will be described later herein). Member 136 is desirably fabricated as a one-piece (unitary) article and may be formed of any suitable flexible material, with a preferred material being injection molded polyvinyl chloride (PVC). As previously mentioned, member 136 has a first end, preferably constructed as a partially yieldable substantially cylindrical socket 246, adapted to be press-fit on and to frictionally receive the outlet coupling 134 of the upper housing portion 132 of the first manifold 124. Pursuant to a preferred construction, the mouth of socket 246 is approximately 0.66 inches in diameter and the outer diameter of the barbed rings 202 of outlet coupling 134 are slightly greater than 0.75 inches whereby the inner surface of socket 246 effects a fluid-tight, friction connection that is highly resistant to detachment under the imposition of tensile force.

The opposite end of member 136 defines a similarly constructed partially yieldable, substantially cylindrical socket 248. The mouth of socket 248, pursuant to a presently preferred design, is approximately 0.77 inches in diameter and frictionally receives the barbed inlet coupling 138 (described hereinafter) of the second manifold 140 having barbed rings whose outer diameter are slightly greater than 0.84 inches in diameter. When press fit upon inlet coupling 138, socket 248 affords a second fluid-tight friction connection also exceptionally resistant to detachment under tensile force.

To prevent kinking or occlusion of the flexible tubular hinge member 136, the moment of inertia is increased significantly in the center of the member. This effect may be achieved by providing a deflection-resistant intermediate region between sockets 246 and 248. Desirably, the deflection-resistant intermediate region is constructed as a crush-resistant abutment member 250. In accordance with the presently preferred embodiment, crush-resistant abutment member 250 which may be a solid member but preferably comprises a pair of spaced apart radially outwardly projecting flanges 252 and 254 which are reinforced and maintained in spaced apart relation by a plurality (preferably four) radially disposed struts or webs 256.

Located on both sides of abutment member 250 between sockets 246 and 248 are "deflection sites" or areas of very low moment of inertia, identified by reference numerals 258 and 260, within which all deflection of the member 136 is localized. Deflection sites 258 and 260 preferably consist of regions where the wall thickness of the tubular member 136 is substantially less than at all other locations therealong. As will be appreciated by reference to FIG. 21, absolute deflection at these sites is limited because, under flexure of the tubular member 136, the crush-resistant abutment member 250 interferes with the bases of the sockets 246 and 248 which receive the couplings 134 and 138.

A further feature of the flexible tubular hinge member 136 is an integral tapered annular flap seal member 262. Flap seal member 262 projects from the base of the socket 248 toward the mouth thereof and is adapted to be inserted into the opening of the inlet coupling 138 of the second manifold 140, as well as into the first leg 144 of the tubular non-breathing valve housing 146 to enhance the fluid seal therewith in a manner to be more fully explained in connection with FIGS. 20 and 21.

Flexible tubular hinge member 136 also satisfies the need for broad angular flexibility (indeed, it permits approximately 180° of flexure in any plane) but does so in a highly compact package. As presently conceived, member 136 has a length of less than about three inches and, preferably, about 2.71 inches. By way of comparison, the flexible corrugated hose 38 in the resuscitator 10 of FIG. 1 is typically about six inches in length. Since overall product length should be minimized to realize optimum apparatus manageability and the concomitant advantage of easier administrability of resuscitation treatment, the construction of member 136 represents a substantial advancement over conventional corrugated hoses which, to achieve similar results in terms of acclusion resistance, require much larger bending radii and, therefore, must be of significantly greater length. Flexible tubular hinge member 136 is especially useful when incorporated into resuscitator apparatus such as apparatus 110, but it should be understood that member 136 may be effectively deployed in any system where a short, kink-resistant, flexible connector is required to fluidly couple the ends of any appropriately sized tubular conduits or similar fluid conducting components.

Figure 17:
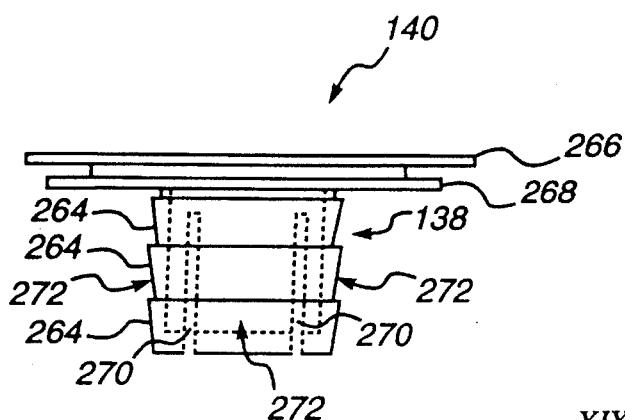
FIG. 17 is an elevational view of a preferred embodiment of a second manifold adapted for use with the squeeze bag resuscitator apparatus of the present invention.
Figure 18:
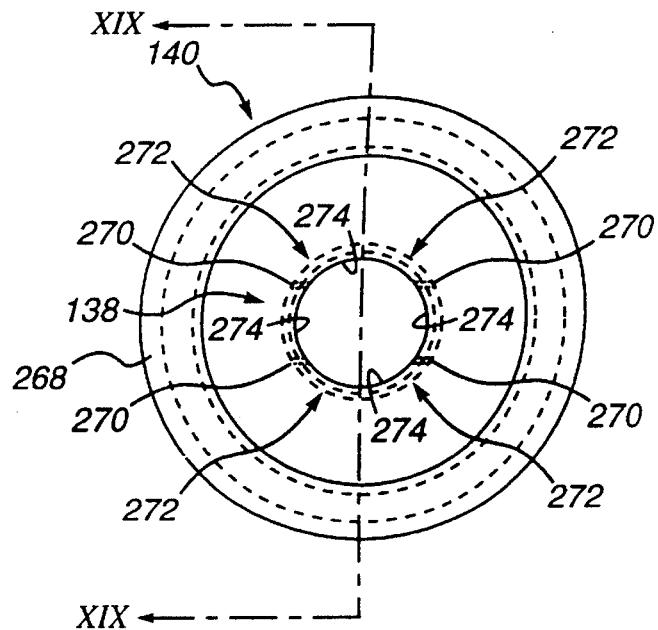
FIG. 18 is a bottom plan view of the second manifold of FIG. 17.
Figure 19:
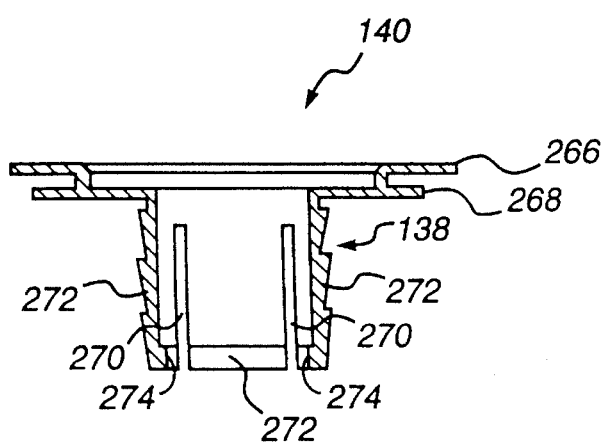
FIG. 19 is an elevational cross-section view of the second manifold taken along line XIX—XIX of FIG. 18.

Referring to FIGS. 17 through 19, a presently preferred embodiment of a second manifold 140 is shown which finds particularly beneficial usage in the resuscitator apparatus 110 of the instant invention. Like flexible tubular hinge member 136, however, the novel features of the second manifold 140 impart to that element broader potential application than simply as a resuscitator apparatus component. It may, for example, be successfully utilized anywhere a low-torque, low-leak, swivel seal must be constructed at the juncture of two tubular conduits or similar fluid conducting elements, particularly when used in conjunction with flexible tubular hinge member 136 as will be more fully appreciated from the discussion of FIGS. 20 and 21.

Second manifold 140, as mentioned previously, is formed with an inlet coupling 138 preferably provided with at least one or, more preferably, a plurality of radially outwardly tapered barbed rings 264 to enhance retention of the socket 248 of the flexible tubular hinge member. And, similar to the upper housing portion 132 of the first manifold 124, second manifold 140 includes a pair of spaced-apart, radially projecting oxygen reservoir bag retaining flanges 266 and 268.

For a substantial portion of its length, inlet coupling 138 is provided with a plurality of slits 270 which separate the coupling into stiff yet resilient collet fingers 272. As most clearly seen in FIG. 19, the mouth of coupling 138 carries a radially inwardly directed annular ring that, by virtue of slits 270, forms a plurality of latch teeth 274 that latchingly engage in a corresponding groove provided in the first leg 144 of the tubular non-breathing valve housing 146 described hereinafter.

Figure 20:
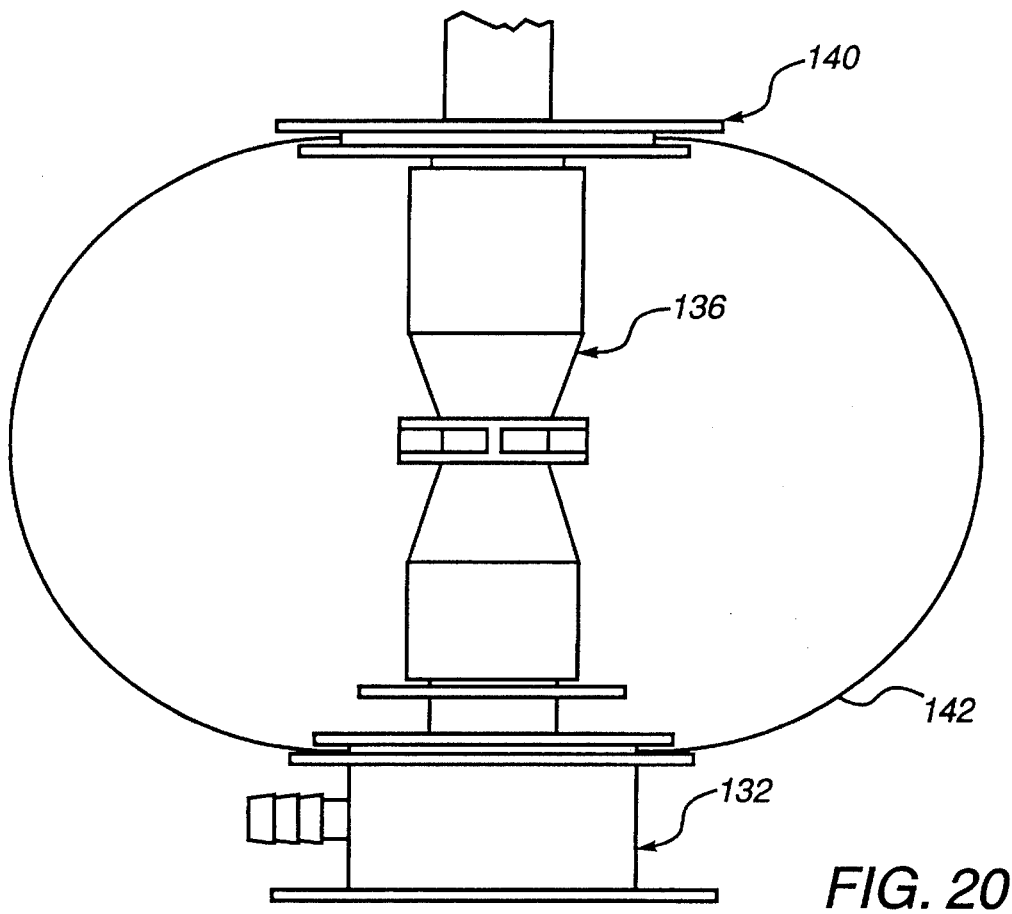
FIG. 20 is an elevational view, in partial section, depicting the connection of a first leg of an L-shaped tubular non-rebreathing valve housing with the second manifold, as well as the connection of the flexible tubular hinge member with both the first and second manifolds.
Figure 21:
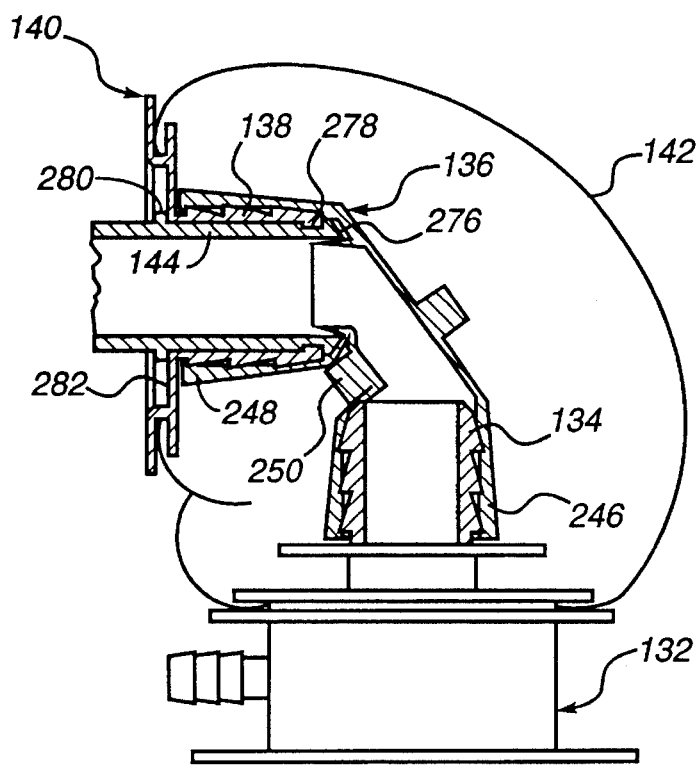
FIG. 21 is a view similar to FIG. 20, in partial section, depicting the flexible tubular hinge member flexed substantially 90° with respect to its unflexed condition shown in FIG. 20.

FIGS. 20 and 21 illustrate in elevational cross-section the assembled state of the upper housing portion 132 of the first manifold 124, the flexible tubular hinge member 136, the upper manifold 14c, the oxygen reservoir bag 142 and the first leg 144 of the tubular non-breathing valve housing 146.

Beginning with the attachment of the oxygen reservoir bag 142 to the first and second manifolds, must initially be noted that the oxygen reservoir bag, as previously stated, is desirably fabricated from thin (preferably 1.0 to 5.0 mil), non-self-restoring, pliable plastic film such as polyurethane, polyethylene or the like. The oxygen reservoir bag is generally oblate in shape and is provided with opposed openings, one adapted for attachment to the first manifold 124, the other to the second manifold 140. More particularly, the lower opening of the oxygen reservoir bag must be stretched over flange 208 of the first manifold upper housing portion 132. Once the flange 208 has been cleared, the bag opening may be released whereby it contracts within the groove formed between flanges 208 and 210 and comes into tight gripping and pneumatic sealing engagement with the first manifold upper housing portion. The opposite end of the oxygen reservoir bag is similarly secured in the groove formed between flanges 266 and 268 of the second manifold 140. As the exterior surfaces of the first and second manifolds in the grooves between flanges 208, 210 and 266, 268 are generally from about 1.5 to 1.7 inches in diameter, the openings at the opposite ends of the oxygen reservoir bag 142 are preferably pre-cut to approximately 0.5 inch in diameter to assure that they snap into contact with the manifold housings. Thus, the oxygen reservoir bag 142 is capable of sealing attachment to the resuscitator apparatus 110 without resort to adhesive tape or other supplemental fastening means.

Flexible tubular hinge member socket 246 is press-fit onto first manifold outlet coupling 134 with flange 204 serving as an abutment preventing overextension of the socket. Likewise, socket 248 is press-fit onto the second manifold inlet coupling 138 with flange 268 acting as an abutment similar to flange 204. Prior to this, however, the first leg 144 of the tubular non-rebreathing valve housing 146 is inserted into the second manifold. Specifically, leg 144 is inserted from behind the flanges 266, 268 through the inlet coupling 138 with a leading beveled edge 276 thereof spreading the collet fingers 272 as it passes latch teeth 274. Immediately behind the beveled edge 276, the circumferential wall of the first leg 144 is formed with an annular groove 278 into which the latch teeth 274 lockingly engage upon passage of the beveled edge. To prevent over-insertion of the first leg, such leg is preferably provided with a suitable stop means 280 such as an annular flange or the like that abuts an annular wall 282 of the second manifold when the latch teeth 274 engage the annular groove 278.

With the assembled inlet coupling 138 and first leg 144 sufficiently and properly inserted into the second socket 248 of the flexible tubular hinge member 136, the tapered annular flap seal member 262 projects into the first leg 144 thereby forming a pocket that sealingly receives the beveled edge 276 and collet fingers 272 yet permits relatively free rotation of the first leg 144 relative to the second manifold 140. As such, a low-torque low-leak, swivel seal is provided without resort to additional and perhaps environmentally unsound sealing means such as gaskets or lubricants. Thus, the tubular housing 146 as well as all components contained therein and attached thereto (e.g., mask 172) may rotate relatively freely with respect to the second manifold 140, whereby adjustability of the resuscitator is completely and safely preserved with minimal loss of oxygen from the system. It will be understood that if it were desirable effect a similar swivel seal between the socket 246 and the first manifold outlet coupling 134, the first manifold upper housing portion 132 could be constructed with a swivel assembly like that associated with the second manifold 140 and the socket 246 of the flexible tubular hinge member could be provided with an annular tapered flap similar to flap 262 adapted to form a pocket for sealingly receiving the distal end of the swivel assembly.

FIG. 21 represents the arrangement of FIG. 20 with the flexible tubular hinge member 136 flexed approximately 90° from its unflexed condition. FIG. 21 exemplifies the manner in which the thin-walled deflection sites 258 and 260 yield under applied deflection force. Yet, because of the proximity of the deflection sites to the barbed couplings 134 and 138, and because of the interference created between the crush-resistant abutment member 250 and those couplings, the flexible tubular hinge member 136 is precluded from bending beyond about 90° in any direction. Consequently, the flow passageway within the tubular member 136 is effectively prevented from occlusion even under the most extreme flexure expected to be encountered under typical resuscitation administration.

FIG. 22 illustrates in elevational cross-section, a first embodiment of a squeeze bag, identified herein by reference numeral 112A, adapted for use with resuscitator apparatus constructed in accordance with the present invention. Squeeze bag 112A has an inlet/outlet opening 116A circumscribed by a bead-type collar 118A. The total internal volume of squeeze bag 112A is about 450–500 cubic inches whereby it finds beneficial application in resuscitation of infants.

Squeeze bag 112B of FIG. 23 represents another embodiment of a removable squeeze bag within the scope of the present invention, its inlet/outlet opening 116B being defined by bead-type collar 118B. The internal volume of squeeze bag 112B is about 850–925 cubic inches and is primarily intended for use in child resuscitation.

A further squeeze bag embodiment having an internal volume of about 1800–2200 cubic inches is depicted in FIG. 24 and identified by reference numeral 112C. A bead-type collar 118C establishes the configuration of its inlet/outlet opening 116C. Squeeze bag 112C is particularly well adapted for resuscitation of adults. In this regard, the diameters of the inlet/outlet openings 116A and 116B of squeeze bags 112A and 112B are preferably about 2.2 to 2.4 inches in diameter, whereas the inlet/outlet opening 116C of bag 112C desirably has a diameter of about 3.0 inches. As a result, it is impossible to mismatch an adult squeeze bag with a resuscitator apparatus adapted for infant or child resuscitation, and vice versa. That is to say, adult squeeze bag 112C will only work with a first manifold 124 having a squeeze bag collar retention groove 120 (FIGS. 2 and 14) sized to mate with collar 118C; and squeeze bags 12A and 112B must be used with first manifolds having squeeze bag retention grooves specifically adapted to receive squeeze bag collars 118A and 118B. Any danger of over-inflation of a child's or infant's airway using an adult sized squeeze bag or, conversely, under-inflation of an adult through the use of an infant's or child's squeeze bag is thus eliminated. As a consequence of a more appropriate match of the squeeze bag to the subject's physical size and/or respiratory requirements, improvements in both the safety and effectiveness of resuscitation therapy are realized.

It is also possible, however, to utilize infant, child and adult squeeze bags having identical inlet/outlet opening diameters with a suitably sized first manifold. Under these circumstances, the operator must exercise caution to select the appropriate squeeze bag for the subject to be resuscitated.

FIGS. 25 through 28 graphically reflect various modalities of the oxygen and air inlet valves of the presently known resuscitator apparatus 10 shown in FIG. 1.

Figure 25:
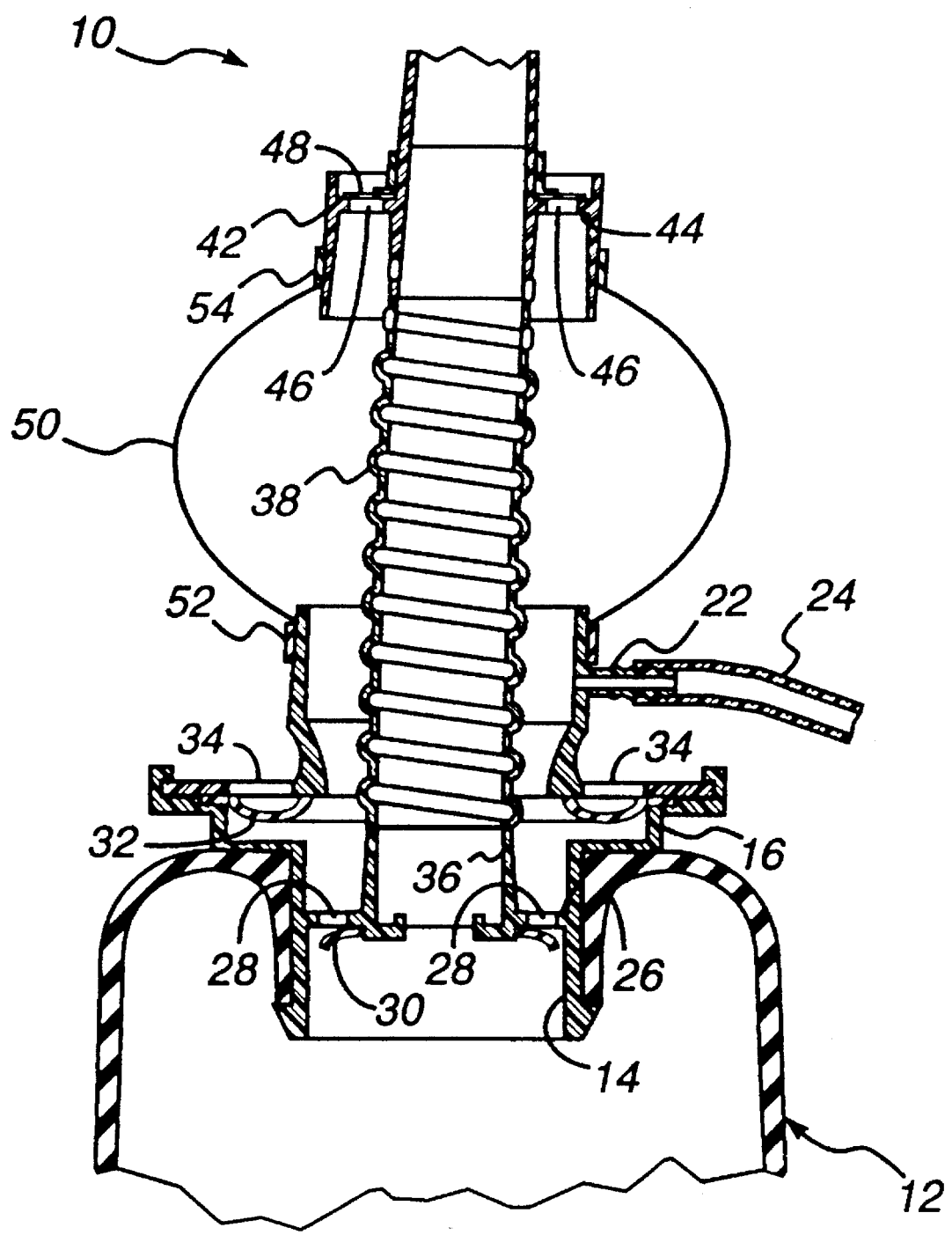
FIGS. 25, 26, 27 and 28 reveal various phases of operation of the oxygen and air inlet valves of the presently known squeeze bag resuscitator apparatus of FIG. 1.

Referring first to FIG. 25, the phase of resuscitation treatment depicted therein may be referred to as "unassisted oxygen administration." During this phase, the subject respires using his own efforts and the operator provides no external assistance such as periodic squeezing and releasing squeeze bag 12. Pressurized oxygen is continuously delivered via flexible conduit 24 through the oxygen inlet coupling and into the interior of the first manifold 18, hence inflating the oxygen reservoir bag 50 in fluid communication therewith.

When the subject inhales, a negative pressure is presented within the squeeze bag 12 thereby drawing the flapper valve 30, as illustrated, from sealing engagement with ports 28 through which the pressurized oxygen may flow to the subject. As inhalation ceases, flapper value 30 closes ports 28, whereby oxygen that has been withdrawn from the oxygen reservoir bag 50 is replenished by new oxygen from the unillustrated oxygen supply. Upon exhalation, as is known, the non-rebreathing valve 64 (FIG. 1) vents the subject's expiratory gases to the atmosphere. Should the subject's rate of respiration be such that there exists prolonged intervals between inhalation, excess oxygen pressure may be vented from the oxygen reservoir bag through ports 46 by overcoming the bias of the second manifold flapper valve 48.

Figure 26:
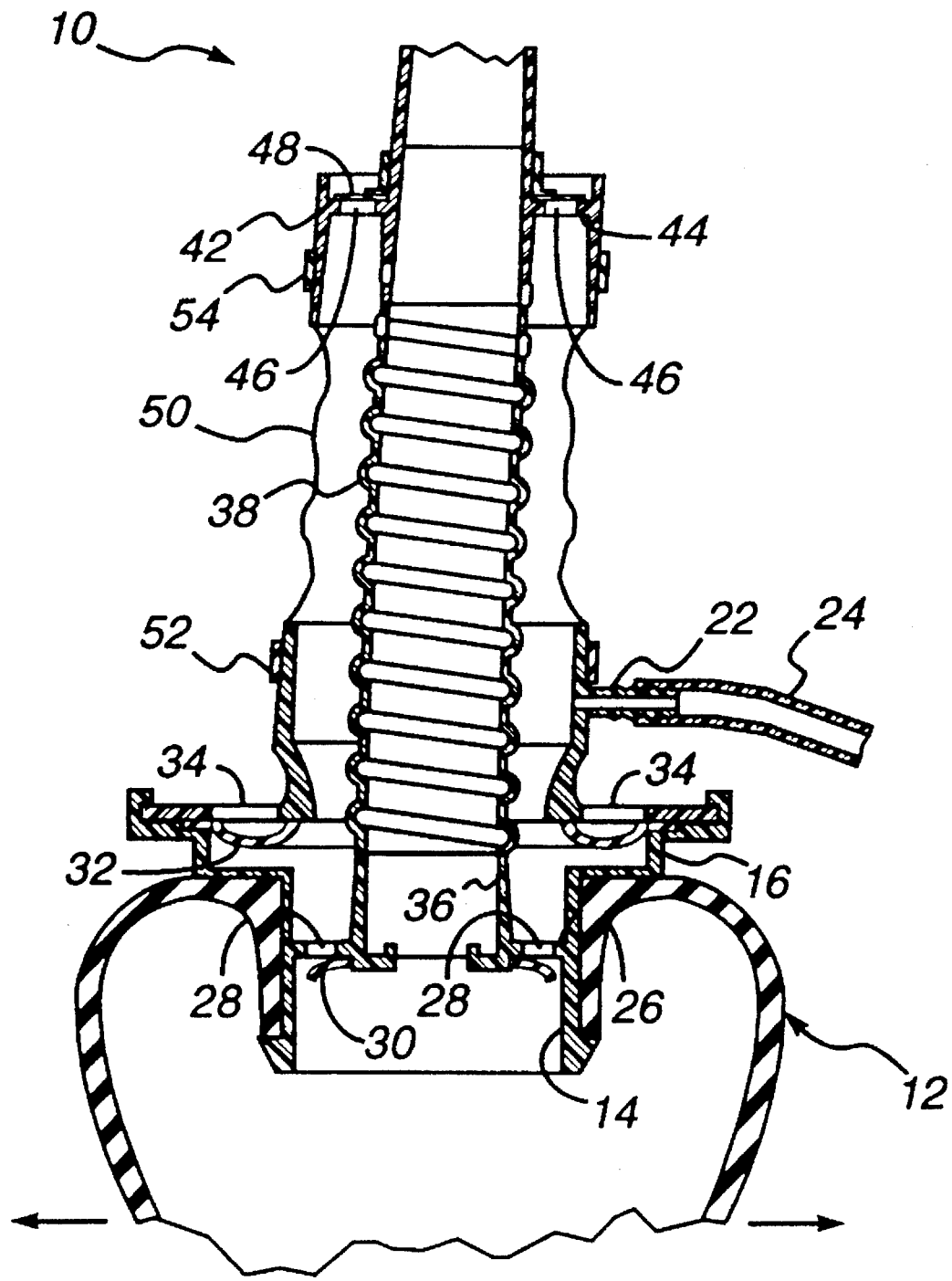

FIG. 26 represents a resuscitation treatment phase that may be categorized as "assisted oxygen administration: squeeze bag decompression." During this phase, the subject is typically exhaling and the operator is releasing squeezing pressure from the walls of the squeeze bag 12. As the squeeze bag is permitted to restore itself, negative pressure is created within the squeeze bag which pulls open the flapper valve 30 and draws oxygen into the squeeze bag from the oxygen reservoir bag thereby deflating the latter.

Figure 27:
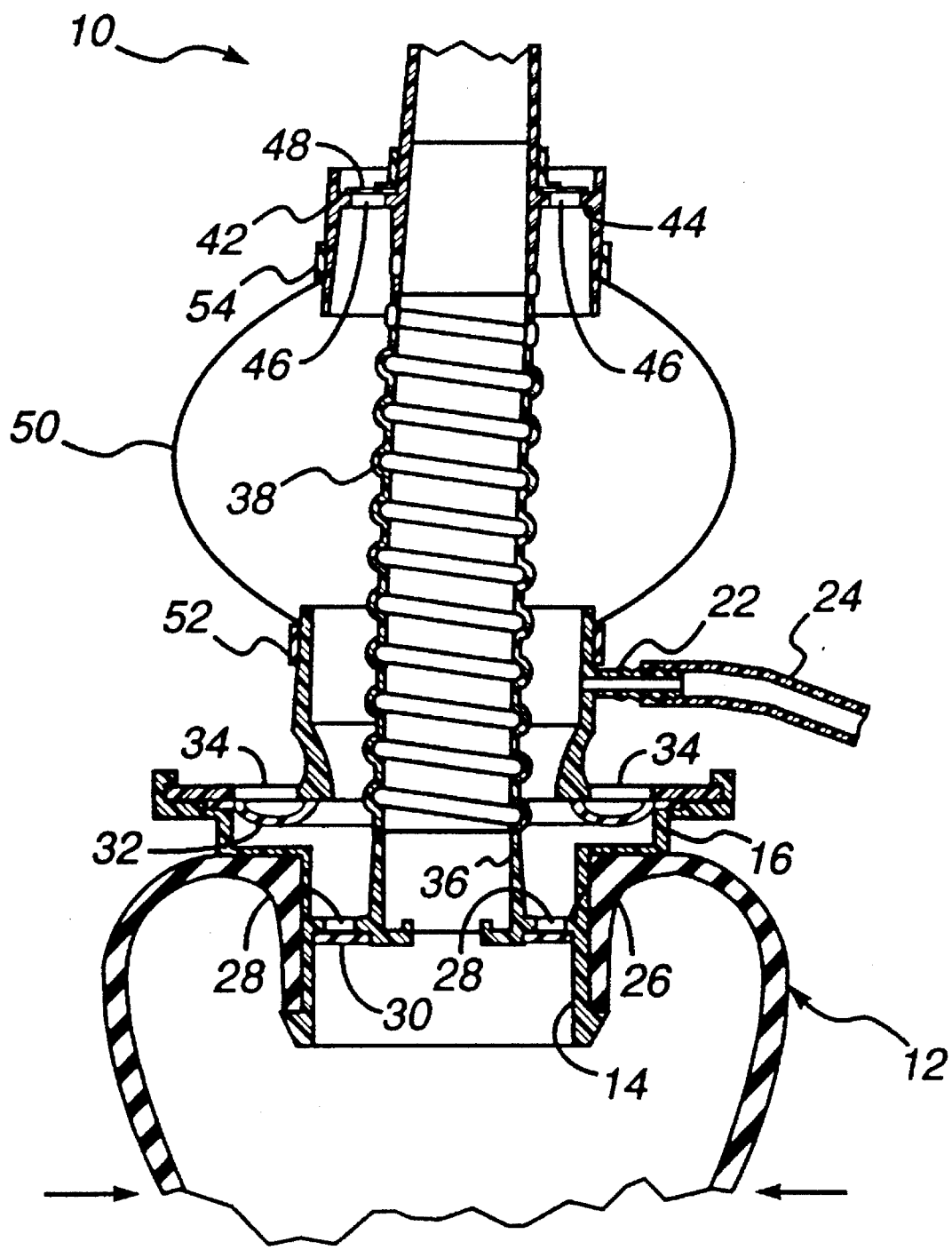

Once the squeeze bag is refilled with oxygen to the operator's satisfaction (which may entail a partial or total release of squeezing force from the walls of the squeeze bag), the resuscitation treatment enters its next phase, i.e., "assisted oxygen administration: squeeze bag compression," exemplified by FIG. 27. At this time the operator squeezes the squeeze bag, hence expelling the contents of the squeeze bag through the flexible hose 38, the non-rebreathing valve 64, the mask 70 and into the subject's airway.

Figure 28:
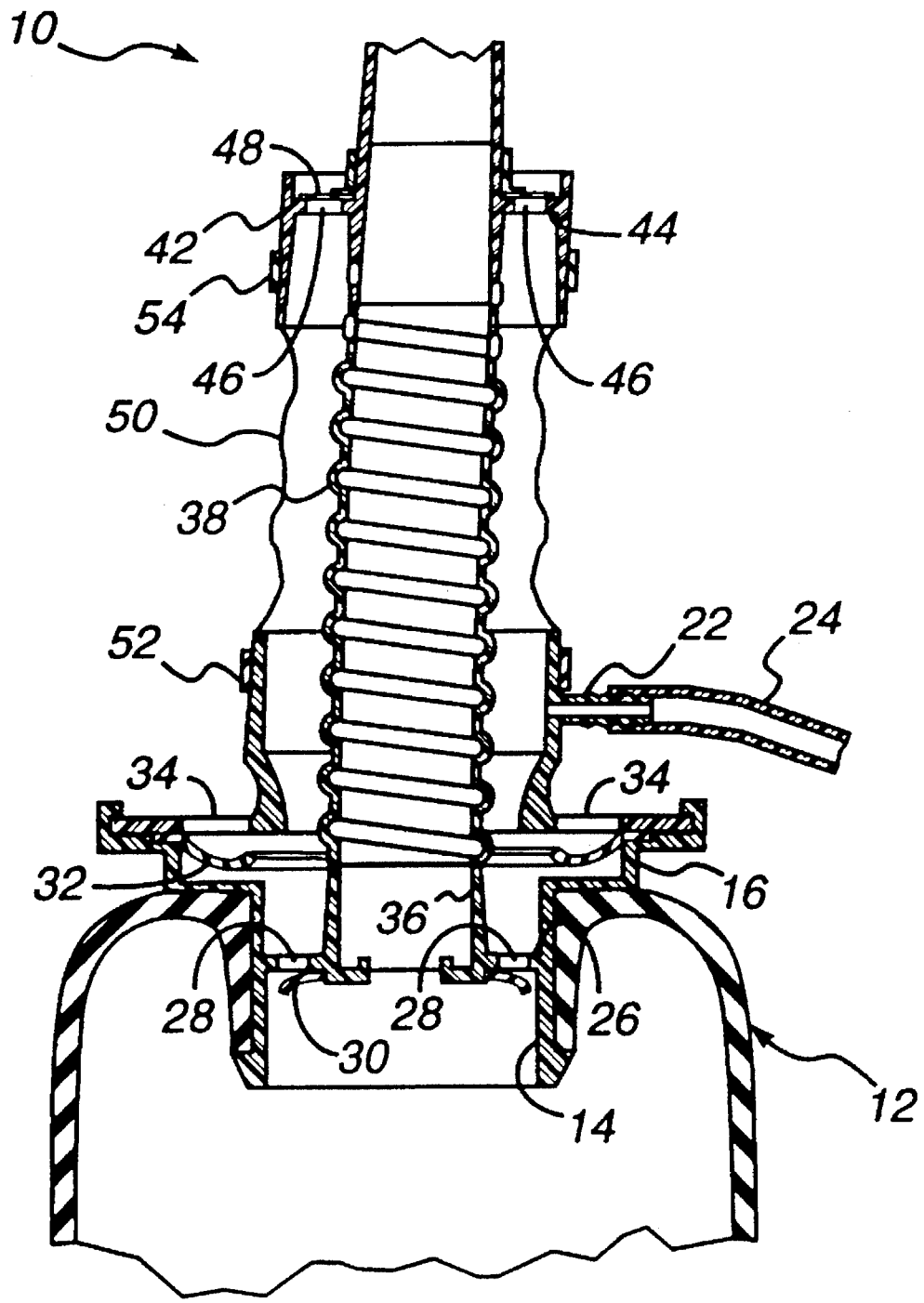
Figure 29:
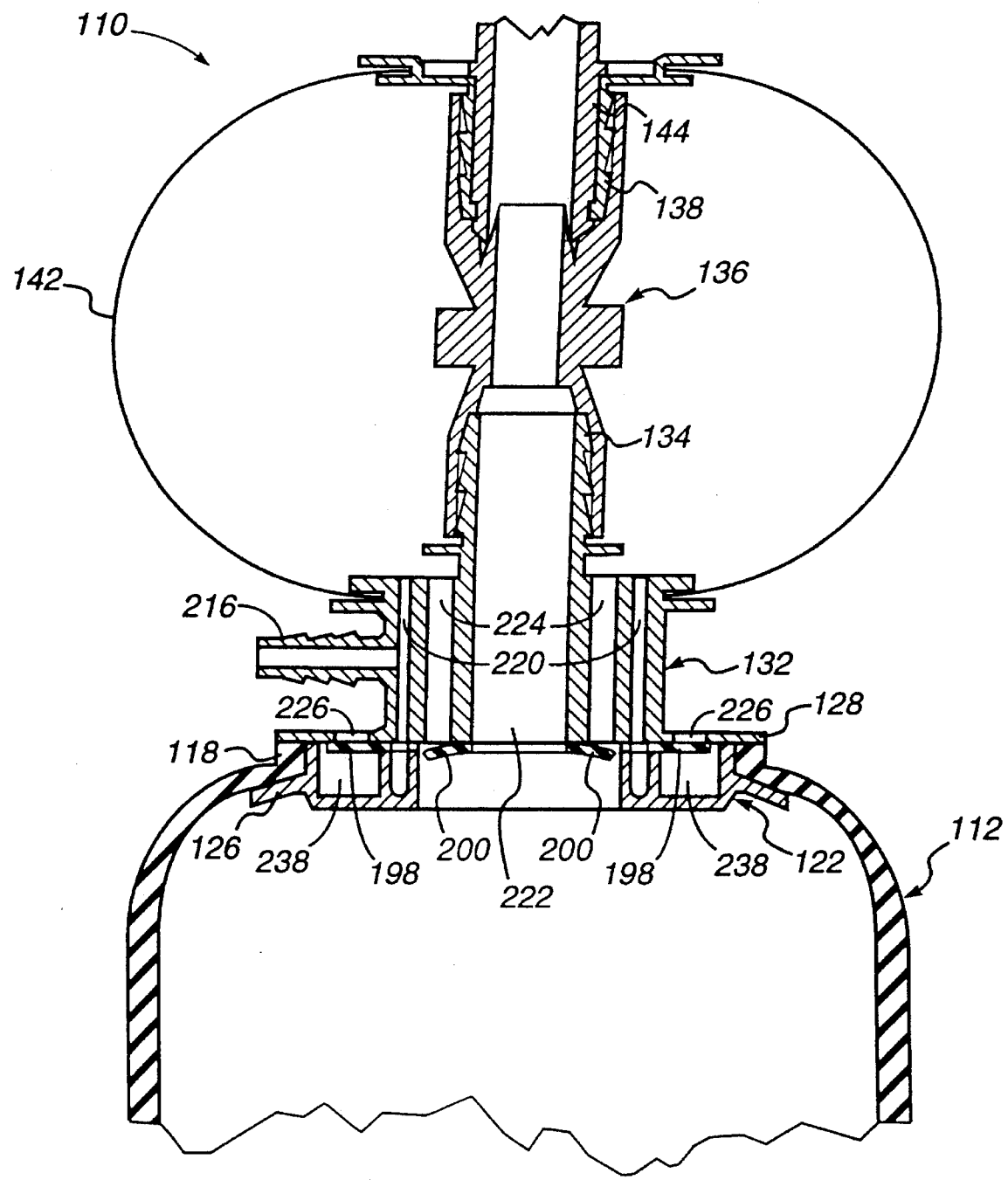
FIGS. 29, 30, 31 and 32 reveal various phases of operation of the substantially unbiased valve means of FIG. 4 as deployed in the squeeze bag resuscitator apparatus of the present invention.

FIG. 28 represents a situation, identified herein as "unassisted ambient air administration" wherein oxygen is no longer being supplied to the resuscitator apparatus 10, either intentionally or unintentionally (e.g., the oxygen supply source becomes depleted or is temporarily interrupted for some other reason). Under these circumstances, in the absence of pressurized oxygen, the subject must inhale ambient atmospheric air. To do so, he must overcome not only the inherent spring bias of the flapper valve 30 but also the significantly greater bias of the semi-toroidal flapper valve 32 (as shown) which normally closes the ambient air inlet ports 34 provided in the first manifold. The semi-toroidal cross-sectional configuration of the flapper valve 32 is deliberately formed therein so as to render the valve sufficiently stiff to resist ingress of atmospheric air through ports 34 under normal oxygen administration conditions, which air would mix with and thereby dilute the desired oxygen concentration.

Should the subject's spontaneous inspiratory efforts be inadequate to actuate both flapper valves 30 and 32, however, and the operator is not keenly aware of and readily responsive to the subject's labored breathing, the presence of the resuscitator apparatus may in fact exacerbate rather than alleviate the subject's respiratory problems.

FIGS. 29 through 32 respectively depict the valve means 130 of the resuscitator apparatus 110 of the present invention as such means would function under the various modes of operation discussed above in connection with FIGS. 25 through 28, namely, "unassisted oxygen administration", "assisted oxygen administration: squeeze bag decompression", "assisted oxygen administration: squeeze bag compression" and "unassisted ambient air administration."

As stated previously, the first valve element 198 and the second valve element 200 of valve means 130 are substantially unbiased and, therefore, in and of themselves, naturally tend to sag from sealing engagement with, respectively, the ambient air inlet ports 226 and the second interior manifold passageways 224. However, under the "unassisted oxygen administration" condition illustrated in FIG. 29 the pressurized oxygen introduced via the oxygen inlet coupling 216 into the first interior passageways 220 exerts oxygen pressure within the manifold chamber 238 which impinges upon the first valve element 198 causing same to close the ambient air inlet ports 226, thereby precluding atmospheric air from passing to the subject during oxygen administration (regardless, incidentally, of whether it be "assisted" or "unassisted" oxygen administration). Simultaneously, the pressurized oxygen inflates the oxygen reservoir bag 142 and flows into the second interior passageways 224, from which a fraction of the pressurized oxygen flows past the second valve element 200 into the squeeze bag 112. Upon its entry into the squeeze bag, the subject may inhale the oxygen essentially without resistance, i.e., encountering only the negligible resistance associated with the inspiratory valve element of the non-rebreathing valve. Thus, under "unassisted oxygen administration," the subject may more freely inhale oxygen than he could while using the resuscitator apparatus of FIG. 1.

Figure 30:
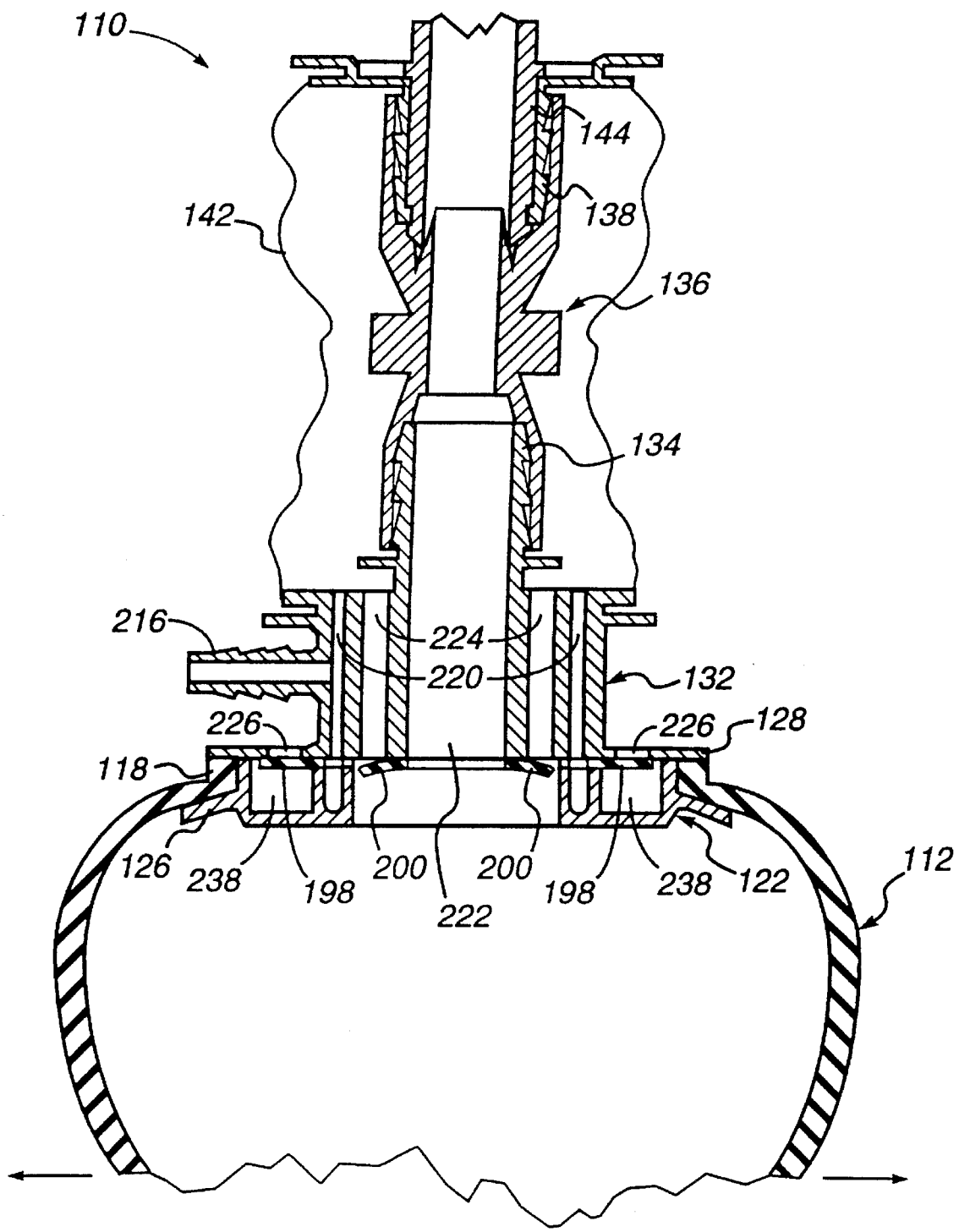

Referring to the "assisted oxygen administration: squeeze bag decompression" phase of FIG. 30, it will be seen that upon self-restoration of squeeze bag 112, the second valve element opens widely responsive to the vacuum created within the squeeze bag whereby oxygen is drawn from the oxygen reservoir bag 142 into the squeeze bag. The subject may exhale during this squeeze bag refilling operation.

The volume of the oxygen reservoir bag 142 is desirably greater than the difference in volume of the squeeze bag between its compressed and restored states. Hence, upon self-restoration of the squeeze bag, residual pressure within the oxygen reservoir bag (assisted in part by the continuous introduction of oxygen through the oxygen inlet 216) is likewise applied in the first manifold chamber 238 at a level sufficient to cause the first valve element 198 to remain in covering and sealing relation with the ambient air inlet ports 226. Consequently, no atmospheric air is permitted to enter the resuscitator during any oxygen administration procedure, whereby the subject receives the full benefits of pure oxygen when such is desired or necessary.

Figure 31:
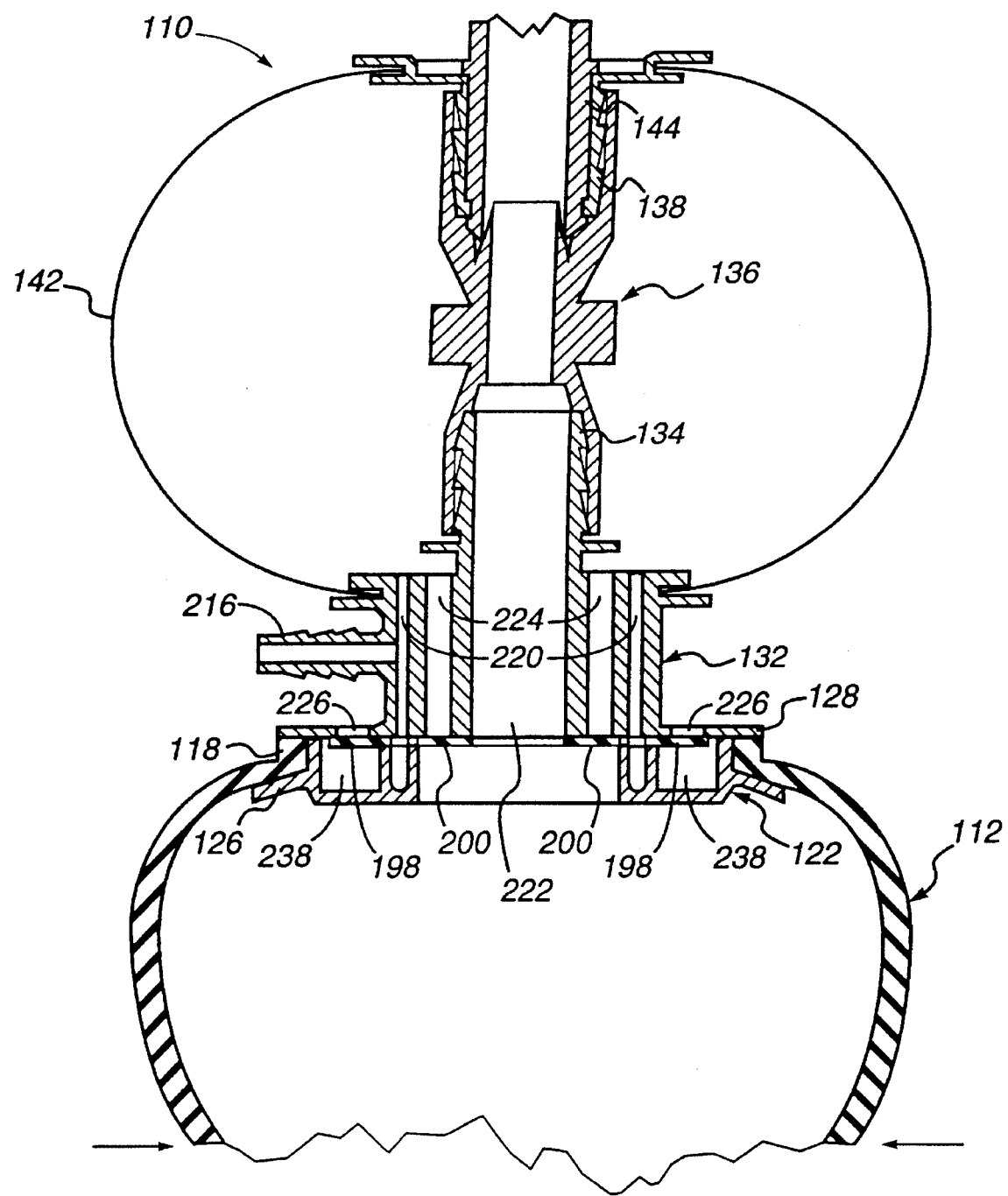

FIG. 31 shows that during the "assisted oxygen administration: squeeze bag compression" phase, with the squeeze bag restored (and during which time the oxygen reservoir bag reinflares with oxygen), the operator squeezes the squeeze bag propelling its contents to the subject in the above-described manner.

Figure 32:
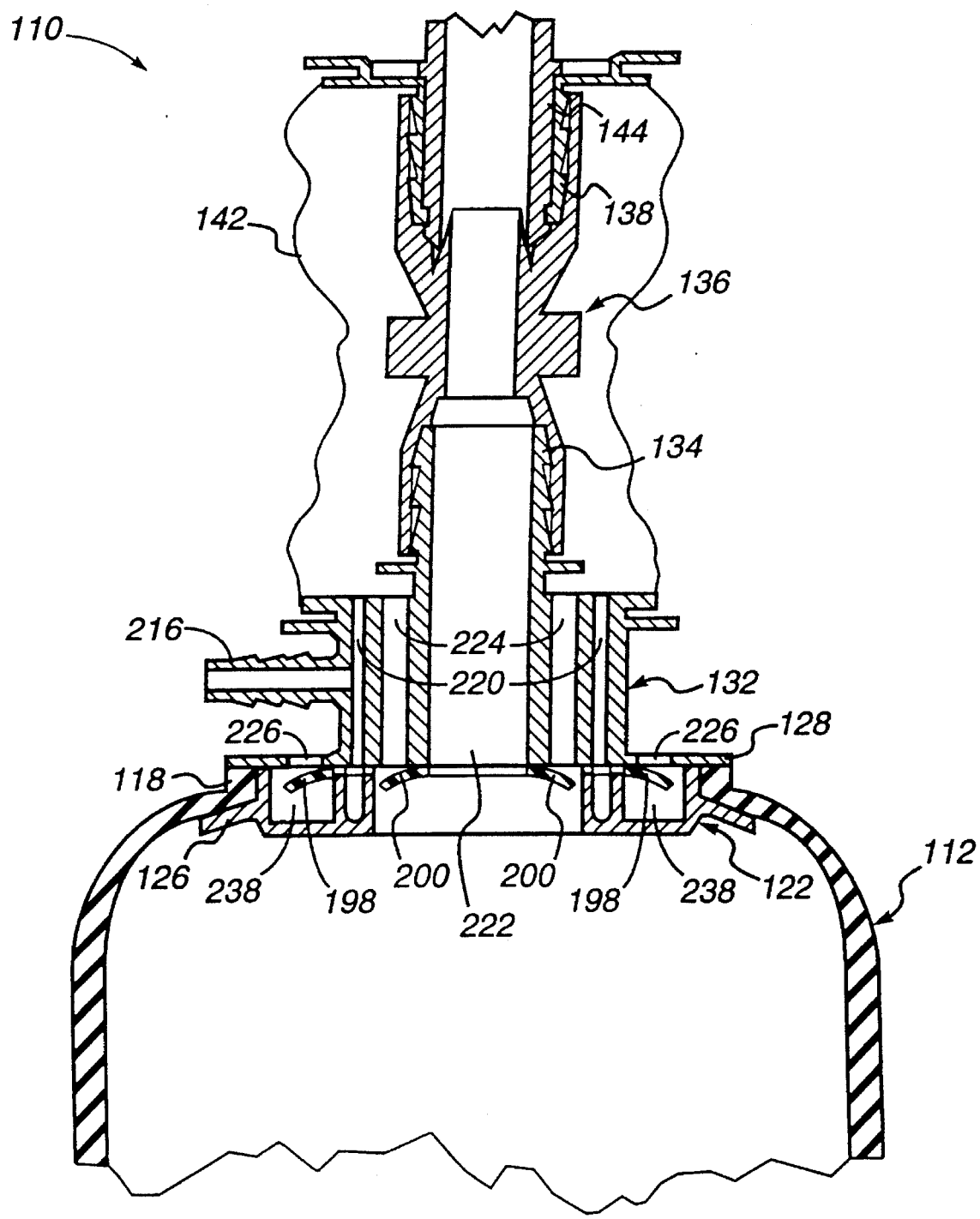

FIG. 32 illustrates what would occur during "unassisted ambient air administration" in the event the oxygen supply should falter. In that event, because the first and second valve elements 198 and 200 are substantially unbiased and tend to sag away from the ambient inlet ports 226 and the second interior manifold passageways 224, the subject may inhale ambient atmospheric air essentially without resistance. More particularly, upon inhalation, atmospheric air may enter the ambient air inlet ports 226, flow around the first valve inlet 198, through the manifold chamber 238 and the first and second interior manifold passageways 220 and 224, past the second valve element 200 and, thereafter through the flexible tubular hinge member 136, the second manifold 140, the non-rebreathing valve and the mask 172. The principle resistance to air flow under these conditions again would be that of the inspiratory valve element of the non-rebreathing valve, which resistance is minimal.

The reader will also appreciate that resuscitator apparatus 110, like its counterpart resuscitator apparatus 10, may also be employed to provide "assisted ambient air administration." That is, if the oxygen supply is interrupted, the operator may periodically squeeze and release the squeeze bag 112 to draw ambient air into the squeeze bag and deliver that air to the subject if conditions dictate that such treatment would be more favorable to treatment of the subject than unassisted ambient air administration.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. An assembly for use in a resuscitator apparatus equipped with a squeeze bag, said squeeze bag having an opening and formed of compressible material, said assembly comprising a first manifold adapted for connection to said squeeze bag opening;

a second manifold;

first tubular means for fluidly coupling said first and second manifolds;

means for providing an interface between said resuscitator apparatus and the airway of a subject; and second tubular means for fluidly coupling said second manifold and said interface means, said second manifold and said second tubular means including means for rotatably coupling said second tubular means to said second manifold, and said first tubular means including means for non-rotatably coupling said first tubular means to said second manifold, and said first tubular means including means for sealingly coupling said first tubular means to said second tubular means and to said second manifold.

2. The assembly of claim 1 wherein said means for rotatably coupling said second manifold to said second tubular means includes cooperating means carried by said second manifold and said second tubular means for latchingly and rotatably coupling said second tubular means to said second manifold.

3. The assembly of claim 2 wherein said means for rotatably coupling said second manifold to said second tubular means includes a groove in said second tubular means, and said cooperating means comprise a plurality of resilient collet fingers formed in said second manifold, said collet fingers including latch teeth for engaging said groove provided in said second tubular means.

4. The assembly of claim 2 wherein said means for sealingly coupling said first tubular means to said second tubular means and to said second manifold comprises a first socket for receiving said first manifold, a second socket for receiving said second manifold, and an annular flap seal member projecting from a base of said second socket toward a mouth thereof, said annular flap seal member extending into said second manifold and operable to enhance sealing between said second socket, said second manifold and said second tubular means.

5. The assembly of claim 4 wherein said annular flap seal member tapers from said base of said second socket toward said mouth thereof.

6. The assembly of claim 1 wherein said means for sealingly coupling said first tubular means to said second tubular means and to said second manifold comprises a first socket for receiving said first manifold, a second socket for receiving said second manifold, and an annular flap seal member projecting from a base of said second socket toward a mouth thereof, said annular flap seal member extending into said second manifold and operable to enhance sealing between said second socket, said second manifold and said second tubular means.

7. The assembly of claim 6 wherein said annular flap seal member tapers from said base of said second socket toward said mouth thereof.

8. A swivel seal assembly comprising:

a manifold;

a first tubular conduit, said manifold and said first tubular conduit including means for non-rotatably coupling said manifold to said first tubular conduit; and a second tubular conduit, said manifold and said second tubular conduit means including means for rotatably coupling said manifold to said second tubular conduit, said first tubular conduit including means for sealingly coupling said first tubular conduit to said manifold and said second tubular conduit.

9. The swivel seal assembly of claim 8 wherein said means for rotatably coupling said manifold to said second tubular conduit includes cooperating means carried by said manifold and said second tubular conduit for latchingly and rotatably coupling said second tubular conduit to said manifold.

10. The swivel seal assembly of claim 9 wherein said means for rotatably coupling said manifold to said second tubular conduit includes a groove in said second tubular conduit, and said cooperating means comprise a plurality of resilient collet fingers formed in said manifold, said collet fingers including latch teeth for engaging in said groove provided in said second tubular conduit.

11. The swivel seal assembly of claim 9 wherein said means for sealingly coupling said first tubular conduit to said manifold and to said second tubular conduit comprises a socket for receiving said manifold and an annular flap seal member projecting from a base of said socket toward a mouth thereof, said annular flap seal member extending into said manifold and operable to enhance sealing between said socket, said manifold and said second tubular conduit.

12. The swivel seal assembly of claim 11 wherein said annular flap seal member tapers from said base of said socket toward said mouth thereof.

13. The swivel seal assembly of claim 8 wherein said means for sealingly coupling said first tubular conduit to said manifold and to said second tubular conduit comprises a socket for receiving said manifold and an annular flap seal member projecting from a base of said socket toward a mouth thereof, said annular flap seal member extending into said manifold and operable to enhance sealing between said socket, said manifold and said second tubular conduit.

14. The swivel seal assembly of claim 13 wherein said annular flap seal member tapers from said base of said socket toward said mouth thereof.

* * * * *